US006984504B2

(12) United States Patent
Hart et al.

(10) Patent No.: US 6,984,504 B2
(45) Date of Patent: Jan. 10, 2006

(54) EBOLA VIRION PROTEINS EXPRESSED FROM VENEZUELAN EQUINE ENCEPHALITIS (VEE) VIRUS REPLICONS

(75) Inventors: Mary K. Hart, Frederick, MD (US); Julie A. Wilson, Frederick, MD (US); Peter Pushko, Frederick, MD (US); Jonathan F. Smith, Sabillasville, MD (US); Alan L. Schmaljohn, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 115 days.

(21) Appl. No.: 10/696,633

(22) Filed: Oct. 29, 2003

(65) Prior Publication Data

US 2004/0146859 A1 Jul. 29, 2004

Related U.S. Application Data

(63) Continuation of application No. 09/337,946, filed on Jun. 22, 1999, now abandoned.
(60) Provisional application No. 60/091,403, filed on Jun. 29, 1998.

(51) Int. Cl.
C12N 15/40 (2006.01)

(52) U.S. Cl. ............... 435/69.3; 435/320.1; 536/23.72; 424/218.1; 530/300; 530/350
(58) Field of Classification Search ............... 435/69.3, 435/320.1; 536/23.72; 530/300, 350; 424/218.1
See application file for complete search history.

(56) References Cited

U.S. PATENT DOCUMENTS

| 6,340,463 B1 | 1/2002 | Mitchell et al. ......... 424/263.1 |
| 2003/0224015 A1 | 12/2003 | Hart et al. |
| 2004/0053865 A1 | 3/2004 | Hart et al. |

FOREIGN PATENT DOCUMENTS

| WO | WO 96/37616 | 11/1996 |
| WO | WO 99/32147 | 7/1999 |
| WO | WO 00/00617 | 1/2000 |
| WO | WO 01/016183 | 3/2001 |

OTHER PUBLICATIONS

Volchkov et al., "The envelope glycoprotein of Ebola virus contains an immunosuppressive–like domain similar to oncogenic retroviruses", FEBS Letters, vol. 305, No. 3, pp. 181–184 (Jul. 1992).
Sanchez et al., "Biochemical Analysis of the Secreted and Virion Glycoproteins of Ebola Virus", J. Virology, Aug. 1998, vol. 72, pp. 6442–6447.
Wilson et al., "Epitopes Involved in Antibody–Mediated Protection from Ebola Virus", Science, vol. 387, Mar. 3, 2000, pp. 1664–1666.
Ichihashi and Oie, "Neutralizing Epitope on Penetration Protein of Vaccinia Virus", Virology 220, pp. 491–494 (1996).
Wolffe et al., "A myristylated membrane protein encoded by the vaccinia virus L1R open reading frame in the target of potent neutralizing monoclonal antibodies", Virology 211, pp. 53–63 (1995).
Roper et al., "Extracellular vaccinia virus envelope glycoprotein encoded by the A33R gene", J. Virology, Jun. 1996, vol. 70, No. 6, pp. 3753–3762.
Isaacs et al., "Characterization of a vaccinia virus–encoded 42–kilodalton class I membrane glycoprotein component of the extracellular virus envelope", J. Virology, Dec. 1992, vol. 66, No. 12, pp. 7217–7224.
Abstract W33–5, "DNA vaccination against poxviruses using combinations of IMV and EEv immunogens", presented Jul. 2000, American Society for Virology Meeting, pp. 113.
Abstract P23–6, "DNA Immunization with the vaccinia L1R and/or A33R genes", Jul. 1998, poster at American Society for Virology meeting.
Meyer et al., "Identification of binding sites for neutralizing monoclonal antibodies on the 14–kDz fuslon protein of orthodox viruses", Virology 200, Short Communications, pp. 778–783 (1994).
Czerny and Mahnel, "Structural and functional analysis of orthopoxvirus epitope with neuralizing monoclonal antibodies", J. General Virology (1990), vol. 71, pp. 2341–2352.
Hooper et al., "DNA vaccination with vaccinia virus L1R and A33R genes protects mice against a lethal poxvirus challenge", Virology 266, pp. 329–339 (2000).
Vazquez and Esteban, "Identification of functional domains in the 14–kilodalton envelope protein (A27L) of vaccinia virus", J. Virology, Nov. 1999, vol. 73, No. 11, pp. 9098–9109.
Vazquez et al., "The vaccinia virus 14–kilodalton (A27L) fusion protein forms a triple coiled–coil structure and interacts with the 21–kilodalton (A17L) virus membrane protein through a C–terminal of alpha–helix", J. Virology, Dec. 1998, vol. 72, No. 12, pp. 10126–10137.
Rodriguez et al., "The vaccinia virus 14–kilodalton fusion proteins forms a stable complex with the processed protein encoded by the vaccinia virus A17L gene", J. Virology, Jun. 1993, vol. 67, No. 6, pp. 3435–3440.

(Continued)

*Primary Examiner*—James Housel
*Assistant Examiner*—Stacy B. Chen
(74) *Attorney, Agent, or Firm*—Elizabeth Arwine

(57) ABSTRACT

Using the Ebola GP, NP, VP24, VP30, VP35 and VP40 virion proteins, a method and composition for use in inducing an immune response which is protective against infection with Ebola virus is described.

4 Claims, 6 Drawing Sheets

OTHER PUBLICATIONS

Lai et al., "The purified 14-kilodalton envelope protein of vaccinia virus produced in *Escherichia coli* induces virus immunity in animals", J. Virology, Oct. 1991, vol. 65, No. 10, pp. 5631–5635.

Rodriguez and Esteban, "Mapping and nucleotide sequence of the vaccinia virus gene that encodes a 14-kilodalton fusion protein," J. Virology, Nov. 1987, vol. 61, No. 11, pp. 3550–3554.

Rodriguez et al., "Isolation and characterization of neutralizing monoclonal antibodies to vaccinia virus", J. Virology, Nov. 1985, vol. 56, No. 2, pp. 482–488.

NCBI PubMed medline, Abstract for Rodriguez et al., "Isolation and characterization of neutralizing monoclonal antibodies to vaccinia virus", J. Virology, Nov. 1985, vol. 56, No. 2, pp. 482–488.

Lin et al., "Vaccinia virus envelope H3L protein binds to cell surface heparan sulfate and is important for intracellular mature virion morphorogenesis and virus infection in vitro and in vivo", J. Virology, Apr. 2000, vol. 74, No. 7, pp. 3353–3365.

Gordon et al., "A prominent antigenic surface polypeptide involved in the biogenesis and function of the vaccinia virus envelope", Virology 181, pp. 671–686 (1991).

Ichihashi et al., "Identification of a vaccinia virus penetration protein", Virology 202, pp. 834–843 (1994).

Demkowicz et al., "Identification and characterization of vaccinia virus genes encoding proteins that are highly antigenic in animals and are Immunodominant in vaccinated humans", J. Virology, Jan. 1992, vol. 66, No. 1, pp. 386–398.

Wilson et al., "Ebola virus: the search for vaccines and treatments", CMLS Cell, Mol. Life Sci, 58 (2001) pp. 1–16.

Pushko et al, "Venezuelan Equine Encephalitis virus replicon vector: Immunogenicity studies with ebola NP and GP genes in guinea pigs", Vaccines 97, Molecular Approaches to the Control of Infectious Diseases, Cold Spring Harbor Laboratory Press, 1997, pp. 253–258.

Geisbert et al., "Evaluation in nonhuman primates of vaccines against Ebola virus", Perspectives, Emerging Infectious Diseases, vol. 8, No. 5, May 2002, pp. 503–507.

Pushko et al., "Recombinant RNA replicons derived from attenuated Venezuelan equine encephalitis virus protect guinea pigs and mice from Ebola hemorrhagic fever virus", Vaccine 11 (2000) pp. 1–12.

Wilson et al., "Vaccine potential of Ebola virus VP24, VP30, VP35, and VP40 proteins", Virology 286, pp. 384–390 (2001).

Wilson and Hart, "Protection for Ebola virus mediated by cytotoxic T lymphocytes specific for the viral nucleoproteins", J. Virology, Mar. 2001, vol. 75, No. 6, pp. 2660–2664.

Maruyama et al., "Recombinant human monoclonal antibodies to Ebola virus", J. Infectious Diseases, 1999, 179 (Suppl 1). pp. S235–S239.

Jahrling et al., "Evaluation of immune globulin and recombinant interferon–alpha2b for treatment of experimental Ebola virus infections", J. Infectious Diseases, 1999, 170 (Suppl 1), pp. S224–S234.

Volchkov et al., "Release of viral glycoproteins during Ebola virus infection", Virology 245, pp. 110–119 (1998).

GenBank, Database printout, for Sanchez et al., Ebola virus nuceoprotein, polymerase copmlex protein (VP35), matrix protein (VP40), glycoprotein (GP), minor nucleoprotein (VP30), and membrane–associates structural protein (VP24), Oct. 14, 1997 (7 pages).

Hevey et al., "Antigenicity and vaccine potential of Marburg virus glycoprotein expressed by baculovirus recombinants", Virology 239, pp. 206–216 (1997).

Maruyama et al., "Ebola virus can be effectively neutralized by antibody produced in natural human infection", J. Virology, Jul. 1999, vol. 73, No. 7, pp. 6024–6030.

Wilson et al., "Ebola virus: the search for vaccines and treatments", CMLS, Cell. Mol. Life Sci. 58 (2001), pp. 1826–1841.

Sanchez et al., "The virion glycoproteins of Ebola viruses are encoded in two reading frames and are expressed through transcriptional editing", PNAS, USA, vol. 93, pp. 3602–3607, Apr. 1996.

Stiles et al., "Production and characterization of monoclonal antibodies against NAJA NAJA ATRA cobrotoxin", Toxicon, vol. 29, No. 10, pp. 1195–1204 (1991).

Feldmann et al., "Marburg virus, a filovirus: messenger RNAs, gene order, and regulatory elements of the replication cycle", Virus Research, 24 (1992) pp. 1–19.

Peters and LeDuc, "An introduction to ebola: the virus nad the disease", J. Infectious Diseases, 1999, vol. 179 (Suppl I), pp. ix–xvi.

Kudoyarova–Zubavichene et al., "Preparation and use of hyperimmune serum for prophylaxis and therapy of ebola virus infections", J. Infectious Diseases, 1999, vol. 179 (Suppl I), pp. S218–223.

Moe et al., "Plaque assay for ebola virus", J. Clinical Microbiology, Apr. 1981, vol. 13, No. 4, pp. 791–793.

Mikhailov et al., "An evaluation of the possibility of ebola fever specific prophylaxis in baboons", Voproxy Virusologii, No. 2, pp. 82–84, 1994.

Harlow and Lane, "Antibodies: A Laboratory Manual", Chapter 6, pp. 210–213 (Cold Spring Harbor Laboratory, New York) 1988.

Schuurs and Van Weemen, "Review" Enzyme–Immunoassay, Clinica Chimica Acta, 81 (1977), pp. 1–40.

Jahrling et al., "Passive Immunization of Ebola virus–infected cynomolgus monkeys with immunoglobulin from hyperimmune horses", Arch Virol, 1996 (Suppl) II, pp. 135–140.

Parren et al., "Pre–and postexposure prophylaxis of ebola virus infectin in an animal model by passive tranfer of a neutraling human antibody," J. Virology, Jun. 2002, vol. 76, No. 12, pp. 6408–6412.

Wilson et al., "Epitopes involved in antobody–mediated protection from ebola virus",Science, vol. 287, pp. 1664–1666, Mar. 3, 2000.

Sanchez et al., "Dectection and molecular characterization of ebola viruses causing disease in human and nonhuman primates", J. Infectious Diseases, 1999, vol. 179 (Suppl. 1), pp. S164–S169.

Sanchez et al., "Biochemical analysis of the secreted and virion glycoproteins of ebola virus", J. Virology, Aug. 1998, vol. 72, No. 8, pp. 6442–6447.

Khaw et al., "Technetium–99m labeling of antibodies to cardiac myosin fab and to human fibrinogen", Radiochemistry and Radiopharmaceuticals, J. Nucl. Med., vol. 23, No. 11, pp. 1011–1019, Nov. 1982.

Farid et al., "Ediotypes, paratopes and molecular mimicry", pp. 1–5, and "An idiotype approach for a vaccine against hepatitus B surface antigen", pp. 285–300, both in Anti–Idiotypes, Receptors, and Molecular Mimicry, Ivy Springer–Verlag, 1988.

Kabat et al., Sequence of proteins of immunological interest, vol. 1, Fifth ed., pp. xiv–xix and 33 pages of sequences (1991).

Waldmann, "Manipulation of T–cell responses with monoclonal antibodies", Ann. Rev. Immunol. (1989) 7:407–444.

Kennedy et al., "Review: Protein–protein coupling reactions and the applications of protein conjugates", Clinics Chimica Acts 70 (1976) pp. 1–31.

"Continuous cultures of fused cells secreting antibody of predefined specificity", Nature, vol. 256, pp. 495–497 (1975).

Volchkov et al., "Processing of the ebola virus glycoprotein by the proprotein convertase furin", PNAS USA, vol. 95, pp. 5762–5767 (May 1998).

Davis et al., "A Viral Vaccine Vector that Expresses Foreign Genes in Lymph Nodes and Protects against Mucosal Challenge", J. Virology, Jun. 1996, vol. 70, No. 6, pp. 3781–3787.

Bray et al., "A Model for Evaluation of Prophylaxis and Therapy of Ebola Hemorrhagic Fever", J. Infectious Deseases, 1998, 178:651–61.

Sullivan et al, "Accelerated vaccination for Ebola virus haemorrhagic fever in non–human primates", Letters to Nature, Nature, vol. 424, Aug. 7, 2003, pp. 681–684.

Sullivan et al., "Development of a preventive vaccine for Ebola virus infection in primates", Letters to Nature, Nature, 2000 (4 pages).

Sanchez et al., "Filoviridae: Marburg and Ebola Viruses", Chapter 40, Fields Virology, 4th Ed., 2001, Lippincott Williams and Wilkins, Philadelphia, editors: Knipe et al, pp. 1249–1304.

Grieder et al., "Specific Restrictions in the PRogression of Venezuelan Equine Encephalitis Virus–Induced Disease Resulting from Single Amino Acid Changes in the Glycoproteins", Virology 206, pp. 994–1006 (1995).

Pushko et al., "Replicon–Helper Systems from Attenuated Venezualan Equine Encephalitis Virus: Expression of Heterologous Genes in Vitro and Immunization against Heterologous Pathogens in Vivo", Virology 239, 389–401 (1997).

Hart et al., "Priming of anti–human immunodeficiency virus (HIV) CD8+ cytotoxic T cells in vivo by carrier–free HIV synthetic peptides", PNAS USA, vol. 88, pp. 9448–9452, Nov. 1991.

Sanchez et al., "Sequence analysis of hte Ebola virus genome: organization, genetic elements, and comparison withthe genome of Marburg virus", Virus Research, 29 (1993) 215–240.

Nicolet and Paulnock, "Promoter Analysis of an Interferon–Inducible Gene Associated with Macrophage Activation", J. Immunology, 1994, pp. 152–162.

Vanderzanden et al., "DNA vaccines expressing either the GP or NP genes of Ebola virus protect mice from lethal challenge", Virology 246, pp. 134–144 (1998).

Sanchez et al., "The nucleoprotein gene of Ebola virus: cloning, sequencing, and in vitro expression", Virology 170, pp. 81–91 (1989).

Volchkov et al., "GP mRNA of Ebola virus is edited by the Ebola virus polymerase and by T7 and vaccinia virus polymerases", Virology 214, pp. 421–430 (1995).

Gilligan, et al., "Assessment of Protective Immunity Conferred by Recombinant Vaccinia Viruses to Guinea Pigs Challenged with Ebola Virus", Vaccines 97, 1997, pp. 87–92.

PCT International Search Report for international application No. PCT/US99/14311 (corresponding to US application serial No. 09/337,946), dated Jun. 14, 2000 (8 pages).

Xu, et al., "Immunization for Ebola virus infection", Nature Medicine, vol. 4, No. 1, Jan. 1998, pp. 37–42.

Vanderzanden, et al., "DNA VAccines Expressing either the GP or NP Genes of Ebola Virus Protech Mice from Lethal Challenge", Virology 246, pp. 134–144 (1998).

(Abstract from Database Biosis, online) Pushko et al., "Venezuelan equine encephalitis virus replicon vector: Immunogenecity studies with ebola NP and GP genes in guinea pigs", document No. XP–0021315176, 1997, 1 page.

Sanchez et al., "Sequence analysis of the Ebola virus genome: organization, genetic elements, and comparison with the genome of Marburg virus", Virus Research, 29 (1993) pp. 215–240.

Sanchez et al., "Variation in the Glycoprotein and VP35 Genes of Marburg Virus Strains", Virology 240, No. 1, 1998, pp. 138–146.

Pushko, et al., "Replicon–Helper Systems from Attenuated Venuzuelan Equine Encephalitis Virus: Expression of Heterologous Genes in Vitro and Immunization against Heterologous Pathogens in Vivo", Virology 239, 1997, pp. 389–401.

FIG. 1

Organization of the Ebola Virus Genome

3' | NP | VP35 | VP40 | GP (sGP) | VP30 | VP24 | L | 5'

NP    Major Nucleocapsid Protein
VP35  Phosphoprotein
VP40  Membrane-Associated Matrix Protein
GP    Transmembrane Glycoprotein
sGP   Secreted Glycoprotein
VP30  Ribonucleoprotein Associated (Minor)
VP24  Membrane-Associated Protein (Minor)
L     RNA-Dependent RNA Polymerase

Ebola Proteins Expressed from VEE Replicons

FIG. 4

EBOLA VIRION PROTEINS EXPRESSED FROM VENEZUELAN EQUINE ENCEPHALITIS (VEE) VIRUS REPLICONS

The application is a continuation application of and claims the benefit of priority to U.S. Ser. No. 09/337,946, filed Jun. 22, 1999, now abandoned. By virtue of U.S. Ser. No. 09/337,946, this application also claims priority from prior U.S. provisional application Ser. No. 60/091,403, filed Jun. 29, 1998.

INTRODUCTION

Ebola viruses, members of the family Filoviridae, are associated with outbreaks of highly lethal hemorrhagic fever in humans and nonhuman primates. The natural reservoir of the virus is unknown and there currently are no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection (FIG. 1). Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) *Virus Res.* 24, 1–19; Sanchez et al., (1993) *Virus Res.* 29, 215–240; reviewed in Peters et al. (1996) In *Fields Virology*, Third ed. pp. 1161–1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) *Proc. Natl. Acad. Sci. USA* 93, 3602–3607; Volchkov et al, (1995) *Virology* 214, 421–430. The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

Recent studies using rodent models to evaluate subunit vaccines for Ebola virus infection using recombinant vaccinia virus encoding Ebola virus GP (Gilligan et al., (1997) In *Vaccines* 97, pp. 87–92. Cold Spring Harbor Laboratory Press, Cold Spring Harbor, N.Y.), or naked DNA constructs expressing either GP or sGP (Xu et al. (1998) *Nature Med.* 4, 37–42) have demonstrated the protective efficacy of Ebola virus GP in guinea pigs. (All documents cited herein supra and infra are hereby incorporated in their entirety by reference thereto.) Additionally, Ebola virus NP and GP genes expressed from naked DNA vaccines (Vanderzanden et al., (1998) *Virology* 246, 134–144) have elicited protective immunity in BALB/c mice. However, successful vaccination of nonhuman primates with individual Ebola virus genes has not been demonstrated. Therefore, there exists a need for a vaccine which is efficacious for protection from Ebola virus infection.

SUMMARY OF THE INVENTION

The present invention satisfies the need discussed above. The present invention relates to a method and composition for use in inducing an immune response which is protective against infection with Ebola virus.

Because the biological functions of the individual Ebola virus proteins are not known and the immune mechanisms necessary for preventing and clearing Ebola virus infection are not well understood, it was not clear which antigens significantly contribute to protection and should therefore be included in an eventual vaccine candidate to induce a protective immune response. We evaluated the ability of packaged Venezuelan equine encephalitis (VEE) virus replicons expressing GP, NP, VP40, VP35, VP30 and VP24 virion proteins of Ebola virus to elicit protective immunity in two strains of mice which differ at the major histocompatibility locus. There are no published reports of the VP proteins having been assayed as antigens for the production of an immune response in a mammal.

The VEE virus replicon (Vrep) is a genetically reorganized version of the VEE virus genome in which the structural protein genes are replaced with a gene from an immunogen of interest, such as the Ebola virus virion proteins. This replicon can be transcribed to produce a self-replicating RNA that can be packaged into infectious particles using defective helper RNAs that encode the glycoprotein and capsid proteins of the VEE virus. Since the packaged replicons do not encode the structural proteins, they are incapable of spreading to new cells and therefore undergo a single abortive round of replication in which large amounts of the inserted immunogen are made in the infected cells. The VEE virus replicon system is described in U.S. patent to Johnston et al., U.S. Pat. No. 5,792,462 issued on Aug. 11, 1998.

For our purposes, each of the Ebola virus genes were individually inserted into a VEE virus replicon vector. The VP24, VP30, VP35, and VP40 genes of Ebola Zaire 1976 (Mayinga isolate) were cloned by reverse transcription of RNA from Ebola-infected Vero E6 cells and viral cDNAs were amplified using the polymerase chain reaction. The Ebola Zaire 1976 (Mayinga isolate) GP and NP genes were obtained from plasmids already containing these genes (Sanchez, A. et al., (1989) *Virology* 170, 81–91; Sanchez, A. et al., (1993) *Virus Res.* 29, 215–240) and were subcloned into the VEE replicon vector.

After characterization of the Ebola gene products expressed from the VEE replicon constructs in cell culture, these constructs were packaged into infectious VEE virus replicon particles (VRPs) and subcutaneously injected into BALB/c and C57BL/6 mice. As controls in these experiments, mice were also immunized with a VEE replicon expressing Lassa nucleoprotein (NP) as an irrelevant control antigen, or injected with PBS buffer alone. The results of this study demonstrate that VRPs expressing the Ebola GP, NP, VP24, VP30, VP35 or VP40 genes induced protection in mice and may provide protection in humans.

Therefore, it is one object of the present invention to provide a DNA fragment encoding each of the Ebola Zaire 1976 GP, NP, VP24, VP30, VP35, and VP40 virion proteins (SEQUENCE ID NOS. 1–7).

It is another object of the present invention to provide the DNA fragments of Ebola virion proteins in a recombinant vector. When the vector is an expression vector, the Ebola virion proteins GP, NP, VP24, VP30, VP35, and VP40 are produced.

It is yet another object of the present invention to provide a VEE virus replicon vector comprising a VEE virus replicon and a DNA fragment encoding any of the Ebola Zaire 1976 (Mayinga isolate) GP, NP, VP24, VP30, VP35, or VP40 proteins. The construct can be used as a nucleic acid vaccine or for the production of self replicating RNA.

It is another object of the present invention to provide a self replicating RNA comprising the VEE virus replicon and any of the Ebola Zaire 1976 (Mayinga isolate) RNAs encoding the GP, NP, VP24, VP30, VP35, and VP40 proteins described above. The RNA can be used as a vaccine for protection from Ebola infection. When the RNA is packaged, a VEE virus replicon particle is produced.

It is another object of the present invention to provide infectious VEE virus replicon particles produced from the VEE virus replicon RNAs described above.

It is further an object of the invention to provide an immunological composition for the protection of subjects against Ebola virus infection, comprising VEE virus replicon particles containing the Ebola virus GP, NP, VP24, VP30, VP35, or VP40 proteins, or any combination of different VEE virus replicons each containing one or more different Ebola proteins selected from GP, NP, VP24, VP30, VP35 and VP40.

BRIEF DESCRIPTION OF THE DRAWINGS

These and other features, aspects, and advantages of the present invention will become better understood with reference to the following description and appended claims, and accompanying drawings where:

FIG. 1 is a schematic description of the organization of the Ebola virus genome.

FIGS. 2A, 2B and 2C are schematic representations of the VEE replicon constructs containing Ebola genes.

FIG. 3 shows the generation of VEE viral-like particles containing Ebola genes.

FIG. 4 is an immunoprecipitation of Ebola proteins produced from replicon constructs.

DETAILED DESCRIPTION

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses (e.g. Ebola Zaire 1976) cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection. The virions of filoviruses contain seven proteins: a membrane-anchored glycoprotein (GP), a nucleoprotein (NP), an RNA-dependent RNA polymerase (L), and four virion structural proteins (VP24, VP30, VP35, and VP40) Little is known about the biological functions of these proteins and it is not known which antigens significantly contribute to protection and should therefore be used in an eventual vaccine candidate.

Replicon. A replicon is equivalent to a full-length virus from which all of the viral structural proteins have been deleted. A multiple cloning site can be inserted downstream of the 26S promoter into the site previously occupied by the structural protein genes. Virtually any heterologous gene may be inserted into this cloning site. The RNA that is transcribed from the replicon is capable of replicating and expressing viral proteins iri a manner that is similar to that seen with the full-length infectious virus clone. However, in lieu of the viral structural proteins, the heterologous antigen is expressed from the 26S promoter in the replicon. This system does not yield any progeny virus particles because there are no viral structural proteins available to package the RNA into particles.

Particles which appear structurally identical to virus particles can be produced by supplying structural protein RNAs in trans for packaging of the replicon RNA. This is typically done with two defective helper RNAs which encode the structural proteins. One helper consists of a full length infectious clone from which the nonstructural protein genes and the glycoprotein genes are deleted. This helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNAs are transcribed in vitro and are co-transfected with replicon RNA. Because the replicon RNA retains the sequences for packaging by the nucleocapsid protein, and because the helpers lack these sequences, only the replicon RNA is packaged by the viral structural proteins. The packaged replicon particles are released from the host cell and can then be purified and inoculated into animals. The packaged replicon particles will have a tropism similar to the parent virus. The packaged replicon particles will infect cells and initiate a single round of replication, resulting in the expression of only the virus nonstructural proteins and the product of the heterologous gene that was cloned in the place of the virus structural proteins. In the absence of RNA encoding the virus structural proteins, no progeny virus particles can be produced from the cells infected by packaged replicon particles.

The Venezuelan equine encephalitis (VEE) virus replicon is a genetically reorganized version of the VEE virus genome in which the genes encoding the VEE structural proteins are replaced with a heterologous gene of interest. In the present invention, the heterologous genes are the GP, NP, or VP virion proteins from the Ebola virus. The result is a sell-replicating RNA that can be packaged into infectious particles using defective helper RNAs that encode the glycoprotein and capsid proteins of the VEE virus. The replicon and its use is further described in U.S. Pat. No. 5,792,462 issued to Johnston et al. on Aug. 11, 1998.

Subject. Includes both human, animal, e.g., horse, donkey, pig, mouse, hamster, monkey, chicken, and insect such as mosquito.

In one embodiment, the present invention relates to DNA fragments which encode any of the Ebola Zaire 1976 (Mayinga isolate) GP, NP, VP24, VP30, VP35, and VP40 proteins. The GP and NP genes of Ebola Zaire were previously sequenced by Sanchez et al. (1993, supra) and have been deposited in GenBank (accession number L11365). A plasmid encoding the VEE replicon vector containing a unique ClaI site downstream from the 26S promoter was described previously (Davis, N. L. et al., (1996) *J. Virol.* 70, 3781–3787; Pushko, P. et al. (1997) *Virology* 239, 389–401). The Ebola GP and NP genes from the Ebola Zaire 1976 virus were derived from PS64— and PGEM3ZF(−)-based plasmids (Sanchez, A. et al. (1989) *Virology* 170, 81–91; Sanchez, A. et al. (1993) *Virus Res.* 29, 215–240). From these plasmids, the BamHI-EcoRI (2.3 kb) and BamHI-KpnI (2.4 kb) fragments containing the NP and GP genes, respectively, were subcloned into a shuttle vector that had been digested with BamHI and EcoRI (Davis et al. (1996) supra; Grieder, F. B. et al. (1995) *Virology* 206, 994–1006). For cloning of the GP gene, overhanging ends produced by KpnI (in the GP fragment) and EcoRI (in the shuttle vector) were made blunt by incubation with T4 DNA polymerase according to methods known in the art. From the shuttle vector, GP or NP genes were subcloned as ClaI-fragments into the ClaI site of the replicon clone, resulting in plasmids encoding the GP or NP genes in place of the VEE structural protein genes downstream from the VEE 26S promoter.

The VP genes of Ebola Zaire were previously sequenced by Sanchez et al. (1993, supra) and have been deposited in GenBank (accession number L11365). The VP genes of Ebola used in the present invention were cloned by reverse transcription of RNA from Ebola-infected Vero E6 cells and subsequent amplification of viral cDNAs using the polymerase chain reaction. First strand synthesis was primed with oligo dT (Life Technologies). Second strand synthesis and subsequent amplification of viral cDNAs were performed with gene-specific primers (SEQ ID NOS:8–16). The primer sequences were derived from the GenBank deposited sequences and were designed to contain a ClaI restriction site for cloning the amplified VP genes into the ClaI site of the replicon vector. The letters and numbers in bold print indicate Ebola gene sequences in the primers and the corresponding location numbers based on the GenBank depositied sequences.

following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The Ebola virus VP24 nucleotide sequence (SEQ ID NO:3) differed from the GenBank sequence at 6 positions, resulting in 3 nonconservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

Two different sequences for the Ebola virus VP30 gene, VP30 and VP30#2 (SEQ ID NOS: 4 and 7) are included.

```
VP24:
(1) forward primer is
5'-GGGATCGATCTCCAGACACCAAGCAAGACC-3'          (SEQ ID NO: 8)
(10,311–10,331)

(2) reverse primer is
5'-GGGATCGATGAGTCAGCATATATGAGTTAGCTC-3'       (SEQ ID NO: 9)
(11,122–11,145)

VP30:
(1) forward primer is
5'-CCCATCGATCAGATCTGCGAACCGGTAGAG-3'          (SEQ ID NO: 10)
(8408–8430)

(2) reverse primer is
5'-CCCATCGATGTACCCTCATCAGACCATGAGC-3'         (SEQ ID NO: 11)
(9347–9368)

VP35:
(1) forward primer is
5'-GGGATCGATAGAAAAGCTGGTCTAACAAGATGA-3'       (SEQ ID NO: 12)
(3110–3133)

(2) reverse primer is
5—CCCATCGATCTCACAAGTGTATCATTAATGTAACGT-3'    (SEQ ID NO: 13)
(4218–4244)

VP40:
(1) forward primer is
5'-CCCATCGATCCTACCTCGGCTGAGAGAGTG-3'          (SEQ ID NO: 14)
(4408–4428)

(2) reverse primer is
5'-CCCATCGATATGTTATGCACTATCCCTGAGAAG-3'       (SEQ ID NO: 15)
(5495–5518)

VP30 #2:
(1) forward primer as for VP30 above
(2) reverse primer is
5'-CCCATCGATCTGTTAGGGTTGTATCATACC-3'          (SEQ ID NO: 16)
```

The Ebola virus genes cloned into the VEE replicon were sequenced. Changes in the DNA sequence relative to the sequence published by Sanchez et al. (1993) are described relative to the nucleotide (nt) sequence number from GenBank (accession number L11365).

The nucleotide sequence we obtained for Ebola virus GP (SEQ ID NO:1) differed from the GenBank sequence by a transition from A to G at nt 8023. This resulted in a change in the amino acid sequence from Ile to Val at position 662 (SEQ ID NO: 17).

The nucleotide sequence we obtained for Ebola virus NP (SEQ ID NO:2) differed from the GenBank sequence at the Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS: 20 and 23). As a result, the C-terminus of the VP30 protein differs significantly from that previously reported. In addition to these 2 changes, the VP30#2 nucleic acid in SEQ ID NO:7 contains a conservative transition from T to C at nt 9217. Because the primers originally used to clone the VP30 gene into the replicon were designed based on the GenBank sequence, the first clone that we constructed (SEQ ID NO: 4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO: 23) did not inhibit the ability of the protein to serve as a protective antigen in BALB/c mice. We are currently examining the ability of the new VEE replicon construct, which we believe contains the authentic C-terminus of VP30 (VP30#2, SEQ ID NO: 23), to protect mice against a lethal Ebola challenge.

The nucleotide sequence for Ebola virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO: 21). The insertion of the T residue resulted in a change in the open reading frame of VP35 from that previously reported by Sanchez et al. (1993) following amino acid number 324. As a result, Ebola virus VP35 encodes a protein of 340 amino acids, where amino acids 325 to 340 (SEQ ID NO: 21) differ from and replace the C-terminal 27 amino acids of the previously published sequence.

Sequencing of VP30 and VP35 was also performed on RT/PCR products from RNA derived from cells that were infected with Ebola virus 1976, Ebola virus 1995 or the mouse-adapted Ebola virus. The changes noted above for the Vrep constructs were also found in these Ebola viruses. Thus, we believe that these changes are real events and not artifacts of cloning.

The Ebola virus VP40 nucleotide sequence (SEQ ID NO:6) differed from the GenBank sequence by a transversion from a C to G at nt 4451 and a transition from a G to A at nt 5081. These sequence changes did not alter the protein sequence of VP40 (SEQ ID NO: 22) from that of the published sequence.

DNA or polynucleotide sequences to which the invention also relates include sequences of at least about 6 nucleotides, preferably at least about 8 nucleotides, more preferably at least about 10–12 nucleotides, most preferably at least about 15–20 nucleotides corresponding, i.e., homologous to or complementary to, a region of the Ebola nucleotide sequences described above. Preferably, the sequence of the region from which the polynucleotide is derived is homologous to or complementary to a sequence which is unique to the Ebola genes. Whether or not a sequence is unique to the Ebola gene can be determined by techniques known to those of skill in the art. For example, the sequence can be compared to sequences in databanks, e.g., GenBank and compared by DNA:DNA hybridization. Regions from which typical DNA sequences may be derived include but are not limited to, for example, regions encoding specific epitopes, as well as non-transcribed and/or non-translated regions.

The derived polynucleotide is not necessarily physically derived from the nucleotide sequences shown in SEQ ID NO:1–7, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays, for example, for the discovery of other Ebola sequences.

In another embodiment, the present invention relates to a recombinant DNA molecule that includes a vector and a DNA sequence as described above. The vector can take the form of a plasmid, a eukaryotic expression vector such as pcDNA3.1, pRcCMV2, pZeoSV2, or pCDM8, which are available from Invitrogen, or a virus vector such as baculovirus vectors, retrovirus vectors or adenovirus vectors, alphavirus vectors, and others known in the art.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of the desired coding sequences when appropriate control sequences which are compatible with the designated host are used.

Among prokaryotic hosts, *E. coli* is the most frequently used host cell for expression. General control sequences for prokaryotes include promoters and ribosome binding sites. Transfer vectors compatible with prokaryotic hosts are commonly derived from a plasmid containing genes conferring ampicillin and tetracycline resistance (for example, pBR322) or from the various pUC vectors, which also contain sequences conferring antibiotic resistance. These antibiotic resistance genes may be used to obtain successful transformants by selection on medium containing the appropriate antibiotics. Please see e.g., Maniatis, Fitsch and Sambrook, *Molecular Cloning; A Laboratory Manual* (1982) *or DNA Cloning*, Volumes I and II (D. N. Glover ed. 1985) for general cloning methods. The DNA sequence can be present in the vector operably linked to sequences encoding an IgG molecule, an adjuvant, a carrier, or an agent for aid in purification of Ebola proteins, such as glutathione S-transferase.

In addition, the Ebola virus gene products can also be expressed in eukaryotic host cells such as yeast cells and mammalian cells. *Saccharomyces cerevisiae, Saccharomyces carlsbergensis*, and *Pichia pastoris* are the most commonly used yeast hosts. Control sequences for yeast vectors are known in the art. Mammalian cell lines available as hosts for expression of cloned genes are known in the art and include many immortalized cell lines available from the American Type Culture Collection (ATCC), such as CHO cells, Vero cells, baby hamster kidney (BHK) cells and COS cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences, poly A addition sequences, enhancer sequences which increase expression, or sequences which cause amplification of the gene. These sequences are known in the art.

The transformed or transfected host cells can be used as a source of DNA sequences described above. When the recombinant molecule takes the form of an expression system, the transformed or transfected cells can be used as a source of the protein described below.

In another embodiment, the present invention relates to Ebola virion proteins such as GP having an amino acid sequence corresponding to SEQ ID NO:17 encompassing 676 amino acids, NP, having an amino acid sequence corresponding to SEQ ID NO:18 encompassing 739 amino acids, VP24, having an amino acid sequence corresponding to SEQ ID NO:19 encompassing 251 amino acids, VP30, having an amino acid sequence corresponding SEQ ID NO:20 encompassing 324 amino acids, VP35, having an amino acid sequence corresponding to SEQ ID NO:21 encompassing 340 amino acids, and VP40, having an amino acid sequence corresponding to SEQ ID NO:22, encompassing 326 amino acids, and VP30#2, having an amino acid sequence corresponding to SEQ ID NO:23 encompassing 288 amino acids, or any allelic variation of the amino acid sequences. By allelic variation is meant a natural or synthetic change in one or more amino acids which occurs between different serotypes or strains of Ebola virus and does not affect the antigenic properties of the protein. There are different strains of Ebola (Zaire 1976, Zaire 1995, Reston, Sudan, and Ivory Coast). The NP and VP genes of these different viruses have not been sequenced. It would be expected that these proteins would have homology among different strains and that vaccination against one Ebola virus strain might afford cross protection to other Ebola virus strains.

A polypeptide or amino acid sequence derived from any of the amino acid sequences in SEQ ID NO:17, 18, 19, 20, 21, 22, and 23 refers to a polypeptide having an amino acid sequence identical to that of a polypeptide encoded in the sequence, or a portion thereof wherein the portion consists of at least 2–5 amino acids, preferably at least 8–10 amino acids, and more preferably at least 11–15 amino acids, or which is immunologically identifiable with a polypeptide encoded in the sequence.

A recombinant or derived polypeptide is not necessarily translated from a designated nucleic acid sequence, or the DNA sequence found in GenBank accession number L11365. It may be generated in any manner, including for example, chemical synthesis, or expression from a recombinant expression system.

Figure 2A:
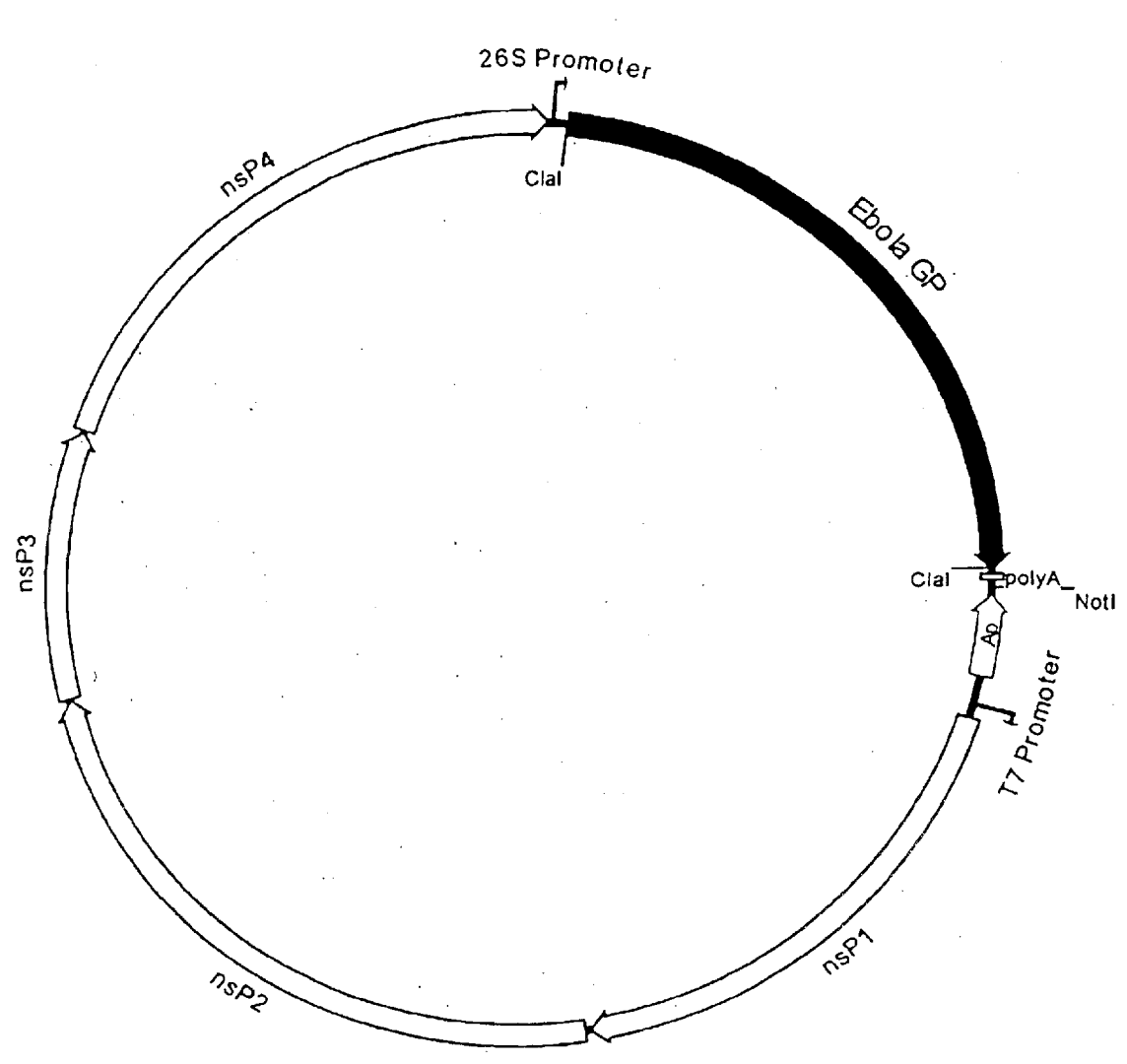
Figure 2B:
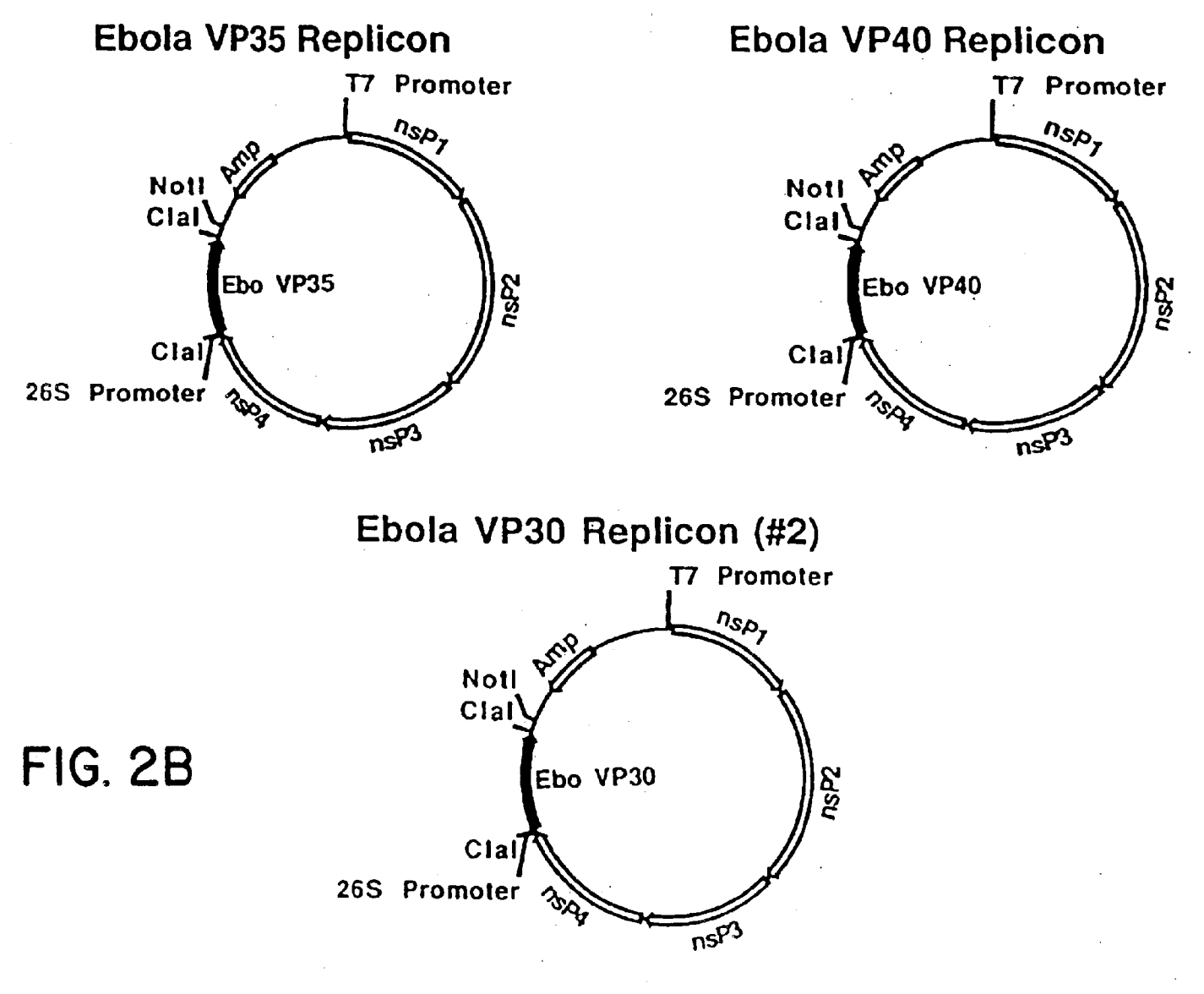
Figure 2C:
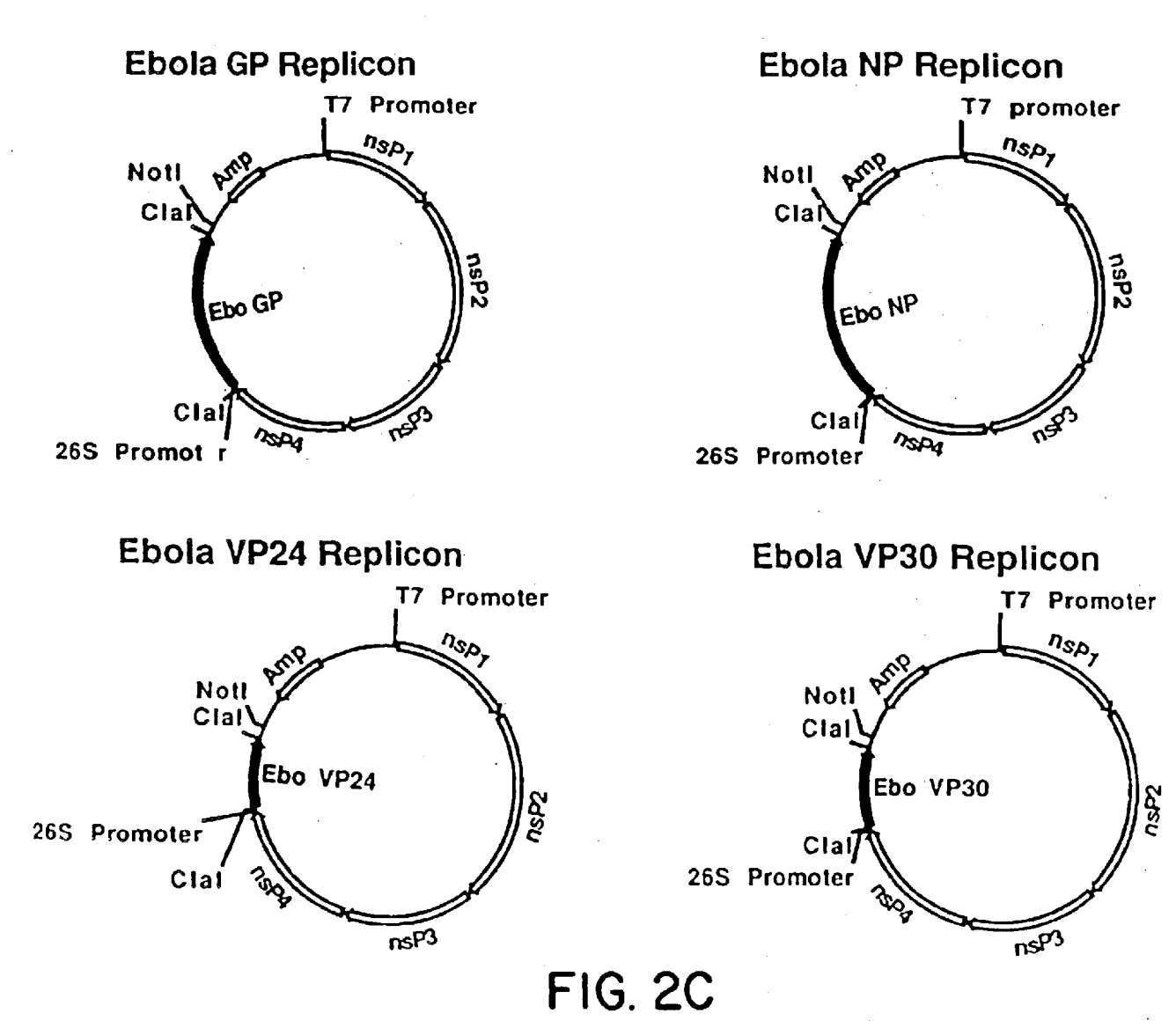
Figure 3:
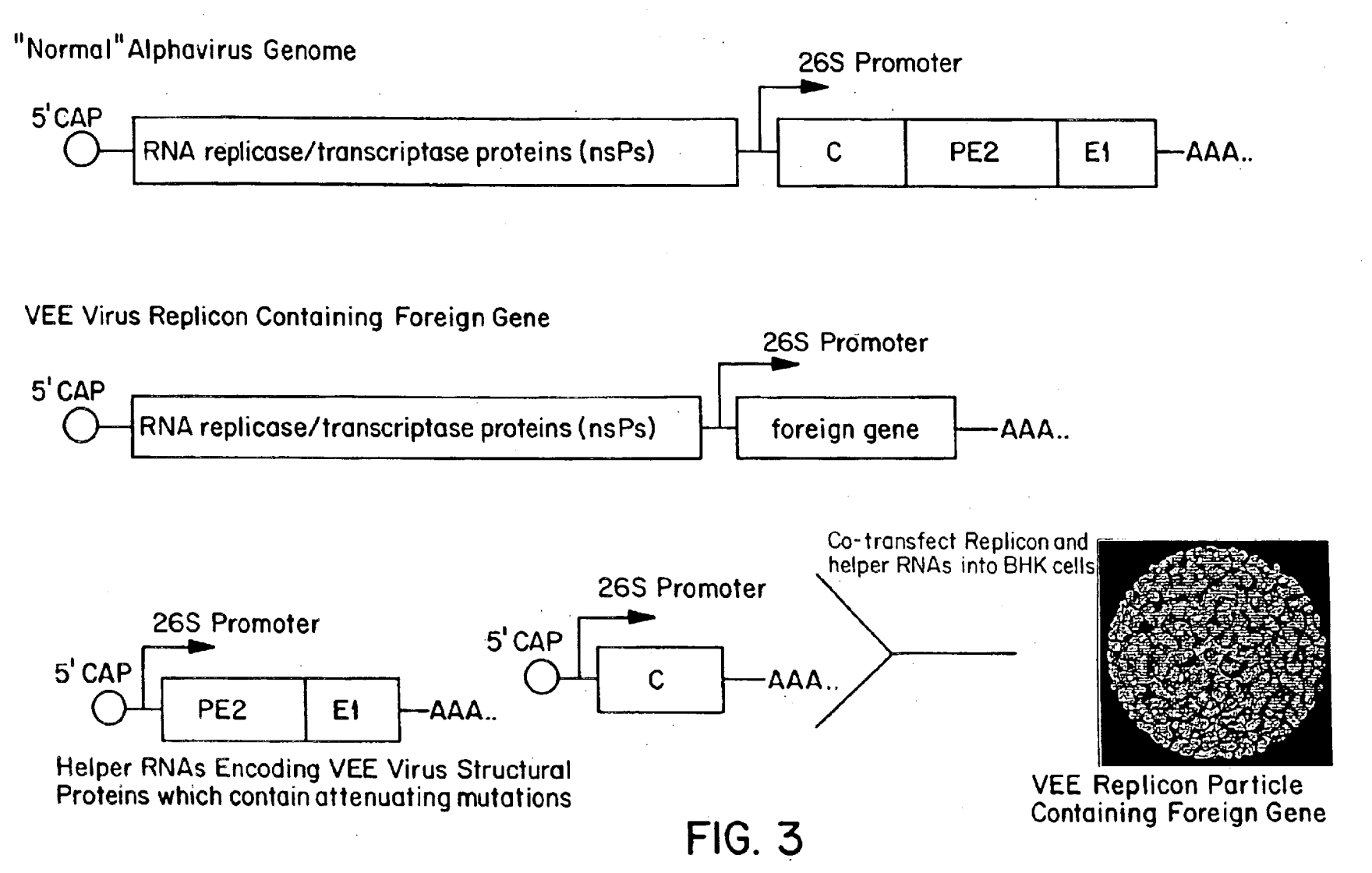

When the DNA or RNA sequences described above are in a replicon expression system, such as the VEE replicon described above, the proteins can be expressed in vivo. The DNA sequence for any of the GP, NP, VP24, VP30, VP35, and VP40 virion proteins can be cloned into the multiple cloning site of a replicon such that transcription of the RNA from the replicon yields an infectious RNA encoding the Ebola protein or proteins of interest (see FIG. 2A, 2B and 2C). The replicon constructs include Ebola virus GP (SEQ ID NO:1) cloned into a VEE replicon (VRepEboGP), Ebola virus NP (SEQ ID NO:2) cloned into a VEE replicon (VRepEboNP), Ebola virus VP24 (SEQ ID NO:3) cloned into a VEE replicon (VRepEboVP24), Ebola virus VP30 (SEQ ID NO:4) or VP30#2 (SEQ ID NO:7) cloned into a VEE replicon (VRepEboVP30 or VRepEboVP30(#2)), Ebola virus VP35 (SEQ ID NO:5) cloned into a VEE replicon (VRepEboVP35), and Ebola virus VP40 (SEQ ID NO:6) cloned into a VEE replicon (VRepEboVP40). The replicon DNA or RNA can be used as a vaccine for inducing protection against infection with Ebola. Use of helper RNAs containing sequences necessary for packaging of the viral replicon transcripts will result in the production of virus-like particles containing replicon RNAs (FIG. 3). These packaged replicons will infect host cells and initiate a single round of replication resulting in the expression of the Ebola proteins in said infected cells. The packaged replicon constructs (i.e. VEE virus replicon particles, VRP) include those that express Ebola virus GP (EboGPVRP), Ebola virus NP (EboNPVRP), Ebola virus VP24 (EboVP24VRP), Ebola virus VP30 (EboVP30VRP or EboVP30VRP(#2)), Ebola virus VP35 (EboVP35VRP), and Ebola virus VP40 (EboVP40VRP).

On Nov. 13, 2003, strain VRepEboVP35 was deposited with the American Type Culture Collection (ATCC®), located at 10801 University Boulevard, Manassas, Va. 20110-2209. VRepEboVP35 has been assigned accession number PTA-5649. The deposit was made under the provisions of the Budapest Treaty, and all restrictions imposed on the availability to the public of the deposited material will be irrevocably removed upon the granting of the patent.

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology*. Frederick M. Ausubel et al. (eds.), John Wiley and Sons, Inc. The RNA molecules can be used, for example, as a direct RNA vaccine, or to transfect cells along with RNA from helper plasmids, one of which expresses VEE glycoproteins and the other VEE capsid proteins, as described above, in order to obtain replicon particles.

In a further embodiment, the present invention relates to a method of producing the recombinant or fusion protein which includes culturing the above-described host cells under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with Ebola or as a diagnostic tool for detection of Ebola infection.

In another embodiment, the present invention relates to antibodies specific for the above-described recombinant proteins (or polypeptides). For instance, an antibody can be raised against a peptide having the amino acid sequence of any of SEQ ID NO:17–25, or against a portion thereof of at least 10 amino acids, preferably, 11–15 amino acids. Persons with ordinary skill in the art using standard methodology can raise monoclonal and polyclonal antibodies to the protein (or polypeptide) of the present invention, or a unique portion thereof. Materials and methods for producing antibodies are well known in the art (see for example Goding, In *Monoclonal Antibodies: Principles and Practice*, Chapter 4, 1986).

In a further embodiment, the present invention relates to a method of detecting the presence of antibodies against Ebola virus in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the Ebola proteins described above or any combination thereof, and contacting it with the serum of a person or animal suspected of having Ebola. The presence of a resulting complex formed between the Ebola protein(s) and serum antibodies specific therefor can be detected by any of the known methods common in the art, such as fluorescent antibody spectroscopy or colorimetry. This method of detection can be used, for example, for the diagnosis of Ebola infection and for determining the degree to which an individual has developed virus-specific Abs after administration of a vaccine.

In yet another embodiment, the present invention relates to a method for detecting the presence of Ebola virion proteins in a sample. Antibodies against GP, NP, and the VP proteins could be used for diagnostic assays. Using standard methodology well known in the art, a diagnostics assay can be constructed by coating on a surface (i.e. a solid support, for example, a microtitration plate or a membrane (e.g. nitrocellulose membrane)), antibodies specific for any of the Ebola proteins described above, and contacting it with serum or a tissue sample of a person suspected of having Ebola infection. The presence of a resulting complex formed between the protein or proteins in the serum and antibodies specific therefor can be detected by any of the known methods common in the art, such as fluorescent antibody spectroscopy or colorimetry. This method of detection can be used, for example, for the diagnosis of Ebola virus infection.

In another embodiment, the present invention relates to a diagnostic kit which contains any combination of the Ebola proteins described above and ancillary reagents that are well known in the art and that are suitable for use in detecting the presence of antibodies to Ebola in serum or a tissue sample. Tissue samples contemplated can be from monkeys, humans, or other mammals.

In yet another embodiment, the present invention relates to DNA or nucleotide sequences for use in detecting the presence of Ebola virus using the reverse transcription-polymerase chain reaction (RT-PCR). The DNA sequence of the present invention can be used to design primers which specifically bind to the viral RNA for the purpose of detecting the presence of Ebola virus or for measuring the amount of Ebola virus in a sample. The primers can be any length ranging from 7 to 400 nucleotides, preferably at least 10 to 15 nucleotides, or more preferably 18 to 40 nucleotides. Reagents and controls necessary for PCR reactions are well known in the art. The amplified products can then be analyzed for the presence of viral sequences, for example by gel fractionation, with or without hybridization, by radiochemistry, and immunochemistry techniques.

In yet another embodiment, the present invention relates to a diagnostic kit which contains PCR primers specific for Ebola virus and ancillary reagents for use in detecting the presence or absence of Ebola in a sample using PCR. Samples contemplated can be obtained from human, animal, e.g., horse, donkey, pig, mouse, hamster, monkey, or other mammals, birds, and insects, such as mosquitoes.

In another embodiment, the present invention relates to an Ebola vaccine comprising VRPs that express one or more of the Ebola proteins described above. The vaccine is administered to a subject wherein the replicon is able to initiate one round of replication producing the Ebola proteins to which a protective immune response is initiated in said subject.

It is likely that the protection afforded by these genes is due to both the humoral (antibodies (Abs)) and cellular (cytotoxic T cells (CTLs)) arms of the immune system. Protective immunity induced to a specific protein may comprise humoral immunity, cellular immunity, or both. The only Ebola virus protein known to be on the outside of the virion is the GP. The presence of GP on the virion surface makes it a likely target for GP-specific Abs that may bind either extracellular virions or infected cells expressing GP on their surfaces. Serum transfer studies in this invention demonstrate that Abs that recognize GP protect mice against lethal Ebola virus challenge.

In contrast, transfer of Abs specific for NP, VP24, VP30, VP35, or VP40 did not protect mice against lethal Ebola challenge. This data, together with the fact that these are internal virion proteins that are not readily accessible to Abs on either extracellular virions or the surface of infected cells, suggest that the protection induced in mice by these proteins is mediated by CTLs.

CTLs can bind to and lyse virally infected cells. This process begins when the proteins produced by cells are routinely digested into peptides. Some of these peptides are bound by the class I or class II molecules of the major histocompatability complex (MHC), which are then transported to the cell surface. During virus infections, viral proteins produced within infected cells also undergo this process. CTLs that have receptors that bind to both a specific peptide and the MHC molecule holding the peptide lyse the peptide-bearing cell, thereby limiting virus replication. Thus, CTLs are characterized as being specific for a particular peptide and restricted to a class I or class II MHC molecule.

CTLs may be induced against any of the Ebola virus proteins, as all of the viral proteins are produced and digested within the infected cell. Thus, protection to Ebola virus could involve CTLs against GP, NP, VP24, VP30, VP35, and/or VP40. It is especially noteworthy that the VP proteins varied in their protective efficacy when tested in genetically inbred mice that differ at the MHC locus. This, together with the inability to demonstrate a role for Abs in protection induced by the VP proteins, strongly supports a role for CTLs. These data also suggest that an eventual vaccine candidate may include several Ebola virus proteins, or several CTL epitopes, capable of inducing broad protection in outbred populations (e.g. people). We have identified two sequences recognized by CTLs. They are Ebola virus NP SEQ ID NO:24 and Ebola virus VP24 SEQ ID NO:25. Testing is in progress to identify the role of CTLs in protection induced by each of these Ebola virus proteins and to define the minimal sequence requirements for the protective response. The CTL assay is well known in the art.

An eventual vaccine candidate might comprise these CTL sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective CTL responses.

In yet another embodiment, the present invention relates to a method for providing immunity against Ebola virus, said method comprising administering one or more VRPs expressing any combination of the GP, NP, VP24, VP30 or VP30#2, VP35 and VP40 Ebola proteins to a subject such that a protective immune reaction is generated.

Vaccine formulations of the present invention comprise an immunogenic amount of a VRP, such as for example EboVP24VRP described above, or, for a multivalent vaccine, a combination of replicons, in a pharmaceutically acceptable carrier. An "immunogenic amount" is an amount of the VRP(s) sufficient to evoke an immune response in the subject to which the vaccine is administered. An amount of from about $10^4$–$10^8$ focus-forming units per dose is suitable, depending upon the age and species of the subject being treated. The subject may be inoculated 2–3 times. Exemplary pharmaceutically acceptable carriers include, but are not limited to, sterile pyrogen-free water and sterile pyrogen-free physiological saline solution.

Administration of the VRPs disclosed herein may be carried out by any suitable means, including parenteral injection (such as intraperitoneal, subcutaneous, or intramuscular injection), in ovo injection of birds, orally, or by topical application of the virus (typically carried in a pharmaceutical formulation) to an airway surface. Topical application of the virus to an airway surface can be carried out by intranasal administration (e.g., by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more DNA constructs or replicating RNA described above can be use in any combination effective to elicit an immunogenic response in a subject. Generally, the nucleic acid vaccine administered may be in an amount of about 1–5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following MATERIALS AND METHODS were used in the examples that follow.

Cells Lines and Viruses

BHK (ATCC CCL 10), Vero 76 (ATCC CRL 1587), and Vero E6 (ATCC CRL 1586) cell lines were maintained in minimal essential medium with Earle's salts, 5–10% fetal bovine serum, and 50 µg/mL gentamicin sulfate. For CTL assays, EL4 (ATCC TIB39), L5178Y (ATCC CRL 1723) and P815 (ATCC TIB64) were maintained in Dulbecco's minimal essential medium supplemented with 5–10% fetal bovine serum and antibiotics.

A stock of the Zaire strain of Ebola virus originally isolated from a patient in the 1976 outbreak (Mayinga) and passaged intracerebrally 3 times in suckling mice and 2 times in Vero cells was adapted to adult mice through serial passage in progressively older suckling mice (Bray et al., (1998) *J. Infect. Dis.* 178, 651–661). A plaque-purified ninth-mouse-passage isolate which was uniformly lethal for adult mice ("mouse-adapted virus") was propagated in Vero E6 cells, aliquotted, and used in all mouse challenge experiments and neutralization assays.

A stock of the Zaire strain of Ebola 1976 virus was passaged spleen to spleen in strain 13 guinea pigs four times. This guinea pig-adapted strain was used to challenge guinea pigs.

Construction and Packaging of Recombinant VEE Virus Replicons (VRPs)

Replicon RNAs were packaged into VRPs as described (Pushko et al., 1997, supra). Briefly, capped replicon RNAs were produced in vitro by T7 run-off transcription of NotI-digested plasmid templates using the RiboMAX T7 RNA polymerase kit (Promega). BHK cells were co-transfected with the replicon RNAs and the 2 helper RNAs expressing the structural proteins of the VEE virus. The cell culture supernatants were harvested approximately 30 hours after transfection and the replicon particles were concentrated and purified by centrifugation through a 20% sucrose cushion. The pellets containing the packaged replicon particles were suspended in PBS and the titers were determined by infecting Vero cells with serial dilutions of the replicon particles and enumerating the infected cells by indirect immunofluorescence with antibodies specific for the Ebola proteins.

Immunoprecipitation of Ebola Virus Proteins Expressed from VEE Virus Replicons

BHK cells were transfected with either the Ebola virus GP, NP, VP24, VP30, VP35, or VP40 replicon RNAS. At 24 h post-transfection, the culture medium was replaced with minimal medium lacking cysteine and methionine, and proteins were labeled for 1 h with $^{35}$S-labeled methionine and cysteine. Cell lysates or supernatants (supe) were collected and immunoprecipitated with polyclonal rabbit anti-Ebola virus serum bound to protein A beads. $^{35}$S-labeled Ebola virus structural proteins from virions grown in Vero E6 cells were also immunoprecipitated as a control for each of the virion proteins. Immunoprecipitated proteins were resolved by electrophoresis on an 11% SDS-polyacrylamide gel and were visualized by autoradiography.

Vaccination of Mice with VEE Virus Replicons

Groups of 10 BALB/c or C57BL/6 mice per experiment were subcutaneously injected at the base of the neck with $2 \times 10^6$ focus-forming units of VRPs encoding the Ebola virus genes. As controls, mice were also injected with either a control VRP encoding the Lassa nucleoprotein (NP) or with PBS. For booster inoculations, animals received identical injections at 1 month intervals. Data are recorded as the combined results of 2 or 3 separate experiments.

Ebola Infection of Mice

One month after the final booster inoculation, mice were transferred to a BSL-4 containment area and challenged by intraperitoneal (ip) inoculation of 10 plaque-forming units (pfu) of mouse-adapted Ebola virus (approximately 300 times the dose lethal for 50% of adult mice). The mice were observed daily, and morbidity and mortality were recorded. Animals surviving at day 21 post-infection were injected again with the same dose of virus and observed for another 21 days.

In some experiments, 4 or 5 mice from vaccinated and control groups were anesthetized and exsanguinated on day 4 (BALB/c mice) or day 5 (C57BL/6 mice) following the initial viral challenge. The viral titers in individual sera were determined by plaque assay.

Passive Transfer of Immune Sera to Naive Mice.

Donor sera were obtained 28 days after the third inoculation with $2 \times 10^6$ focus-forming units of VRPs encoding the indicated Ebola virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted Ebola virus.

Vaccination and Challenae of Guinea Pigs.

EboGPVRP or EboNPVRP ($1 \times 10^7$ focus-forming units in 0.5 ml PBS) were administered subcutaneously to inbred strain 2 or strain 13 guinea pigs (300–400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge. Guinea pigs were challenged on day 56 (strain 2) or day 160 (strain 13) by subcutaneous administration of 1000 $LD_{50}$ ($1 \times 10^4$ PFU) of guinea pig-adapted Ebola virus. Animals were observed daily for 60 days, and morbidity (determined as changes in behavior, appearance, and weight) and survival were recorded. Blood samples were taken on the days indicated after challenge and viremia levels were determined by plaque assay.

Virus titration and neutralization assay. Viral stocks were serially diluted in growth medium, adsorbed onto confluent Vero E6 cells in 6- or 12-well dishes, incubated for 1 hour at 37° C., and covered with an agarose overlay (Moe, J. et al. (1981) *J. Clin. Microbiol.* 13:791–793). A second overlay containing 5% neutral red solution in PBS or agarose was added 6 days later, and plaques were counted the following day. Pooled pre-challenge serum samples from some of the immunized groups were tested for the presence of Ebola-neutralizing antibodies by plaque reduction neutralization assay. Aliquots of Ebola virus in growth medium were mixed with serial dilutions of test serum, or with normal serum, or medium only, incubated at 37° C. for 1 h, and used to infect Vero E6 cells. Plaques were counted 1 week later.

Cytotoxic T cell assays. BALB/c and C57BL/6 mice were inoculated with VRPs encoding Ebola virus NP or VP24 or the control Lassa NP protein. Mice were euthanized at various times after the last inoculation and their spleens removed. The spleens were gently ruptured to generate single cell suspensions. Spleen cells ($1 \times 10^6$/ml) were cultured in vitro for 2 days in the presence of 10–25 $\mu$M of peptides synthesized from Ebola virus NP or VP24 amino acid sequences, and then for an additional 5 days in the presence of peptide and 10% supernatant from concanavalin A-stimulated syngeneic spleen cells. Synthetic peptides were made from Ebola virus amino acid sequences predicted by a computer algorithm (HLA Peptide Binding Predictions, Parker, K. C., et al. (1994) *J. Immunol.* 152:163) to have a likelihood of meeting the MHC class I binding requirements of the BALB/c ($H-2^d$) and C57BL/6 ($H-2^b$) haplotypes. Only 2 of 8 peptides predicted by the algorithm and tested to date have been identified as containing CTL epitopes. After in vitro restimulation, the spleen cells were tested in a standard $^{51}$chromium-release assay well known in the art (see, for example, Hart et al. (1991) *Proc. Natl. Acad. Sci. USA* 88: 9449–9452). Percent specific lysis of peptide-coated, MHC-matched or mismatched target cells was calculated as:

$$\frac{\text{Experimental cpm} - \text{Spontaneous cpm} \times 100}{\text{Maximum cpm} - \text{Spontaneous cpm}}$$

Spontaneous cpm are the number of counts released from target cells incubated in medium. Maximum cpm are obtained by lysing target cells with 1% Triton X-100. Experimental cpm are the counts from wells in which target cells are incubated with varying numbers of effector (CTL) cells. Target cells tested were L5178Y lymphoma or P815 mastocytoma cells (MHC matched to the $H2^d$ BALB/c mice and EL4 lymphoma cells (MHC matched to the $H2^b$ C57BL/6 mice). The effector:target (E:T) ratios tested were 25:1, 12:1, 6:1 and 3:1.

EXAMPLE 1

Survival Of Mice Inoculated With VRPs Encoding Ebola Proteins. Mice were inoculated two or three times at 1 month intervals with $2 \times 10^6$ focus-forming units of VRPs encoding individual Ebola virus genes, or Lassa virus NP as a control, or with phosphate buffered saline (PBS). Mice were challenged with 10 pfu of mouse-adapted Ebola virus one month after the final immunization. The mice were observed daily, and morbidity and mortality data are shown in Table 1A for BALB/c mice and Table 1B for C57BL/6 mice. The viral titers in individual sera of some mice on day 4 (BALB/c mice) or day 5 (C57BL/6 mice) following the initial viral challenge were determined by plaque assay.

TABLE 1

Survival Of Mice Inoculated With VRPs Encoding Ebola Proteins

| VRP | #Injections | S/T[1] (%) | MDD[2] | V/T[3] | Viremia[4] |
|---|---|---|---|---|---|
| A. BALB/c Mice | | | | | |
| EboNP | 3 | 30/30 (100%) | 5/5 | 5.2 | |
| | 2 | 19/20 (95%) | 7 | 5/5 | 4.6 |
| EboGP | 3 | 15/29 (52%) | 8 | 1/5 | 6.6 |
| | 2 | 14/20 (70%) | 7 | 3/5 | 3.1 |
| EboVP24 | 3 | 27/30 (90%) | 8 | 5/5 | 5.2 |
| | 2 | 19/20 (95%) | 6 | 4/4 | 4.8 |
| EboVP30 | 3 | 17/20 (85%) | 7 | 5/5 | 6.2 |
| | 2 | 11/20 (55%) | 7 | 5/5 | 6.5 |
| EboVP35 | 3 | 5/19 (26%) | 7 | 5/5 | 6.9 |
| | 2 | 4/20 (20%) | 7 | 5/5 | 6.5 |
| EboVP40 | 3 | 14/20 (70%) | 8 | 5/5 | 4.6 |
| | 2 | 17/20 (85%) | 7 | 5/5 | 5.6 |
| LassaNP | 3 | 0/29 (0%) | 7 | 5/5 | 8.0 |
| | 2 | 0/20 (0%) | 7 | 5/5 | 8.4 |
| none (PBS) | 3 | 1/30 (3%) | 6 | 5/5 | 8.3 |
| | 2 | 0/20 (0%) | 6 | 5/5 | 8.7 |
| B. C57BL/6 Mice | | | | | |
| EboNP | 3 | 15/20 (75%) | 8 | 5/5 | 4.1 |
| | 2 | 8/10 (80%) | 9 | ND[5] | ND |
| EboGP | 3 | 19/20 (95%) | 10 | 0/5 | — |
| | 2 | 10/10 (100%) | — | ND | ND |
| EboVP24 | 3 | 0/20 (0%) | 7 | 5/5 | 8.6 |
| EboVP30 | 3 | 2/20 (10%) | 8 | 5/5 | 7.7 |
| EboVP35 | 3 | 14/20 (70%) | 8 | 5/5 | 4.5 |

TABLE 1-continued

Survival Of Mice Inoculated With VRPs Encoding Ebola Proteins

| VRP | #Injections | S/T[1] (%) | MDD[2] | V/T[3] | Viremia[4] |
|---|---|---|---|---|---|
| EboVP40 | 3 | 1/20 (5%) | 7 | 4/4 | 7.8 |
| LassaNP | 3 | 1/20 (5%) | 7 | 4/4 | 8.6 |
|  | 2 | 0/10 (0%) | 7 | ND | ND |
| none (PBS) | 3 | 3/20 (15%) | 7 | 5/5 | 8.6 |
|  | 2 | 0/10 (0%) | 7 | ND | ND |

[1]S/T, Survivors/total challenged.
[2]MDD, Mean day to death
[3]V/T, Number of mice with viremia/total number tested.
[4]Geometric mean of $Log_{10}$ viremia titers in PFU/mL. Standard errors for all groups were 1.5 or less, except for the group of BALB/c mice given 2 inoculations of EboGP, which was 2.2.
[5]ND, not determined.

EXAMPLE 2

VP24-Immunized BALB/c Mice Survive A High-Dose Challenge With Ebola Virus.

BALB/c mice were inoculated two times with $2\times10^6$ focus-forming units of EboVP24VRP. Mice were challenged with either $1\times10^3$ pfu or $1\times10^5$ pfu of mouse-adapted Ebola virus 1 month after the second inoculation. Morbidity and mortality data for these mice are shown in Table 2.

TABLE 2

VP24-Immunized BALB/c Mice Survive A High-Dose Challenge With Ebola virus

| Replicon | Challenge Dose | Survivors/Total |
|---|---|---|
| EboVP24 | $1 \times 10^3$ pfu ($3 \times 10^4$ $LD_{50}$) | 5/5 |
| EboVP24 | $1 \times 10^5$ pfu ($3 \times 10^6$ $LD_{50}$) | 5/5 |
| None | $1 \times 10^3$ pfu ($3 \times 10^4$ $LD_{50}$) | 0/4 |
| None | $1 \times 10^5$ pfu ($3 \times 10^6$ $LD_{50}$) | 0/3 |

EXAMPLE 3

Passive Transfer Of Immune Sera Can Protect Naive Mice From A Lethal Challenge Of Ebola Virus.

Donor sera were obtained 28 days after the third inoculation with $2\times10^6$ focus-forming units of VRPs encoding the indicated Ebola virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted Ebola virus.

TABLE 3

Passive Transfer of Immune Sera Can Protect Unvaccinated Mice from a Lethal Challenge of Ebola Virus

|  | Survivors/Total | Mean Day of Death |
|---|---|---|
| A. BALB/c Mice Specificity of Donor Sera⁻ |  |  |
| Ebola GP | 15/20 | 8 |
| Ebola NP | 1/20 | 7 |
| Ebola VP24 | 0/20 | 6 |
| Ebola VP30 | 0/20 | 7 |
| Ebola VP35 | ND[1] | ND |
| Ebola VP40 | 0/20 | 6 |
| Lassa NP | 0/20 | 7 |
| Normal mouse sera | 0/20 | 6 |
| B. C57BL/6 Mice Specificity of Donor Sera⁻ |  |  |
| Ebola GP | 17/20 | 7 |
| Ebola NP | 0/20 | 7 |
| Ebola VP24 | ND | ND |
| Ebola VP30 | ND | ND |
| Ebola VP35 | 0/20 | 7 |
| Ebola VP40 | ND | ND |
| Lassa NP | 0/20 | 7 |
| Normal mouse sera | 0/20 | 7 |

[1]ND, not determined

EXAMPLE 4

Immunogenicity and Efficacy of VRepEboGP and VRepEboNP in Guinea Pigs.

EboGPVRP or EboNPVRP ($1\times10^7$ IU in 0.5 ml PBS) were administered subcutaneously to inbred strain 2 or strain 13 guinea pigs (300–400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge.

Sera from vaccinated animals were assayed for antibodies to Ebola by plaque-reduction neutralization, and ELISA. Vaccination with VRepEboGP or NP induced high titers of antibodies to the Ebola proteins (Table 4) in both guinea pig strains. Neutralizing antibody responses were only detected in animals vaccinated with the GP construct (Table 4).

Guinea pigs were challenged on day 56 (strain 2) or day 160 (strain 13) by subcutaneous administration of 1000 $LD_{50}$ ($10^4$ PFU) of guinea pig-adapted Ebola virus. Animals were observed daily for 60 days, and morbidity (determined as changes in behavior, appearance, and weight) and survival were recorded. Blood samples were taken on the days indicated after challenge and viremia levels were determined by plaque assay. Strain 13 guinea pigs vaccinated with the GP construct, alone or in combination with NP, survived lethal Ebola challenge (Table 4). Likewise, vaccination of strain 2 inbred guinea pigs with the GP construct protected 3/5 animals against death from lethal Ebola challenge, and significantly prolonged the mean day of death (MDD) in one of the two animals that died (Table 4). Vaccination with NP alone did not protect either guinea pig strain.

TABLE 4

Immunogenicity and efficacy of VRepEboGP and VRepEboNP in guinea pigs

| VRP | ELISA[a] | PRNT$_{50}$ | Survivors/ total (MDD[b]) | Viremia[c] d7 | d14 |
|---|---|---|---|---|---|
| A. Strain 2 guinea pigs ||||||
| GP | 4.1 | 30 | 3/5 (13 + 2.8) | 2.3 | 1.8 |
| NP | 3.9 | <10 | 0/5 (9.2 + 1.1) | 3.0 | — |
| Mock | <1.5 | <10 | 0/5 (8.8 + 0.5) | 3.9 | — |
| B. Strain 13 guinea pigs ||||||
| GP | 4.0 | 140 | 5/5 | <2.0 | <2.0 |
| GP/NP | 3.8 | 70 | 5/5 | <2.0 | <2.0 |
| NP | 2.8 | <10 | 1/5 (8.3 + 2.2) | 4.6 | — |
| Lassa NP | <1.5 | <10 | 2/5 (8.3 + 0.6) | 4.8 | — |

[a]Data are expressed as geometric mean titers, log$_{10}$.
[b]MDD, mean day to death
[c]Geometric mean of log$_{10}$ viremia titers in PFU/mL. Standard errors for all groups were 0.9 or less.

EXAMPLE 5

Induction of murine CTL Responses to Ebola Virus NP and Ebola Virus VP24 Proteins.

BALB/c and C57BL/6 mice were inoculated with VRPs encoding Ebola virus NP or VP24. Mice were euthanized at various times after the last inoculation and their spleens removed. Spleen cells (1×10$^6$/ml) were cultured in vitro for 2 days in the presence of 10 to 25 µM of peptides, and then for an additional 5 days in the presence of peptide and 10% supernatant from concanavalin A-stimulated syngeneic spleen cells. After in vitro restimulation, the spleen cells were tested in a standard $^{51}$chromium-release assay. Percent specific lysis of peptide-coated, MHC-matched or mismatched target cells was calculated as:

$$\frac{\text{Experimental cpm} - \text{Spontaneous cpm}}{\text{Maximum cpm} - \text{Spontaneous cpm}} \times 100$$

In the experiments shown, spontaneous release did not exceed 15%.

TABLE 5

Induction of murine CTL responses to Ebola virus NP and Ebola virus VP24 proteins.

| Mice, VRP[1] | Peptide[2] | Cell[3] | % Specific Lysis E:T ratio 25 |
|---|---|---|---|
| BALB/c, VP24 | None | P815 | 55 |
| BALB/c, VP24 | SEQ ID NO: 25 | P815 | 93 |
| C57BL/6, EboNP | None | EL4 | 2 |
| C57BL/6, EboNP[4] | SEQ ID NO: 24 | EL4 | 70 |
| C57BL/6, EboNP | Lassa NP | EL4 | 2 |
| C57BL/6, LassaNP | None | L5178Y | 1 |
| C57BL/6, LassaNP | SEQ ID NO: 24 | L5178Y | 0 |

TABLE 5-continued

Induction of murine CTL responses to Ebola virus NP and Ebola virus VP24 proteins.

| Mice, VRP[1] | Peptide[2] | Cell[3] | % Specific Lysis E:T ratio 25 |
|---|---|---|---|
| C57BL/6, LassaNP | None | EL4 | 2 |
| C57BL/6, LassaNP | SEQ ID NO: 24 | EL4 | 6 |

[1]Indicates the mouse strain used and the VRP used as the in vivo immunogen. In vitro restimulation was performed using SEQ ID NO: 24 peptide for BALB/c mice and SEQ ID NO: 23 for all C57BL/6 mice shown.
[2]Indicates the peptide used to coat the target cells for the chromium release assay.
[3]Target cells are MHC-matched to the effector cells, except for the L5178Y cells that are C57BL/6 mismatched.
[4]High levels of specific lysis (>40%) were also observed using E:T ratios of 12, 6, 3, or 1:1.

RESULTS AND DISCUSSION

Figure 4:
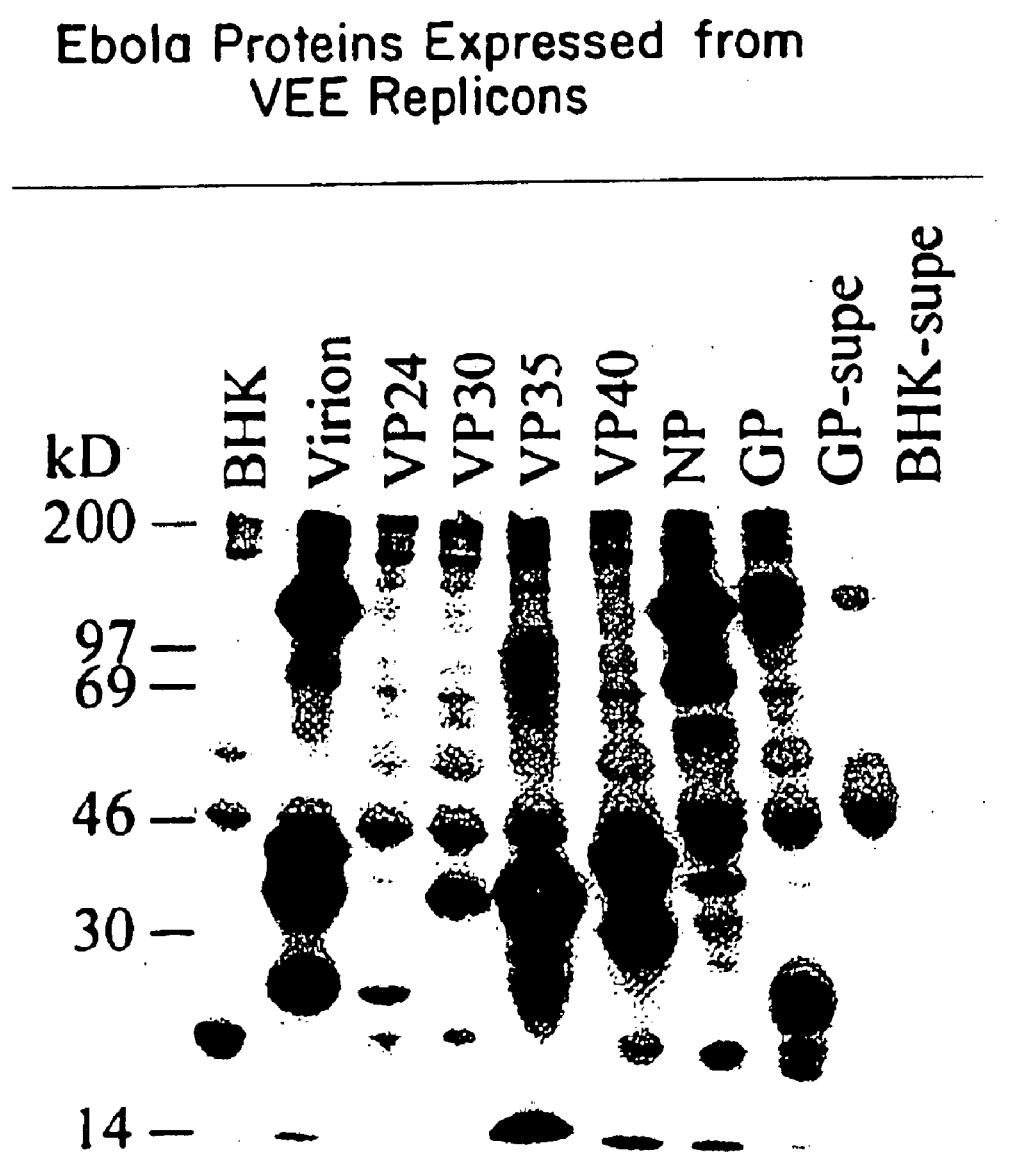

Ebola Zaire 1976 (Mayinga) virus causes acute hemorrhagic fever characterized by high mortality. There are no current vaccines or effective therapeutic measures to protect individuals who are exposed to this virus. In addition, it is not known which genes are essential for evoking protective immunity and should therefore be included in a vaccine designed for human use. In this study, the GP, NP, VP24, VP30, VP35, and VP40 virion protein genes of the Ebola Zaire 1976 (Mayinga) virus were cloned and inserted into a Venezuelan equine encephalitis (VEE) virus replicon vector (VRep) as shown in FIGS. 2A and 2B. These VReps were packaged as VEE replicon particles (VRPs) using the VEE virus structural proteins provided as helper RNAs, as shown in FIG. 3. This enables expression of the Ebola virus proteins in host cells. The Ebola virus proteins produced from these constructs were characterized in vitro and were shown to react with polyclonal rabbit anti-Ebola virus antibodies bound to Protein A beads following SDS gel electrophoresis of immunoprecipitated proteins (FIG. 4).

The Ebola virus genes were sequenced from the VEE replicon clones and are listed here as SEQ ID NO:1 (GP), 2 (NP), 3 (VP24), 4 (VP30), 5 (VP35), 6 (VP40), and 7 (VP30#2) as described below. The corresponding amino acid sequences of the Ebola proteins expressed from these replicons are listed as SEQ ID NO: 17, 18, 19, 20, 21, 22, and 23, respectively. Changes in the DNA sequence relative to the sequence published by Sanchez et al. (1993) are described relative to the nucleotide (nt) sequence number from GenBank (accession number L11365).

The sequence we obtained for Ebola virus GP (SEQ ID NO:1) differed from the GenBank sequence by a transition from A to G at nt 8023. This resulted in a change in the amino acid sequence from Ile to Val at position 662 (SEQ ID NO: 17).

The DNA sequence we obtained for Ebola virus NP (SEQ ID NO:2) differed from the GenBank sequence at the following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The Ebola virus VP24 (SEQ ID NO:3) gene differed from the GenBank sequence at 6 positions, resulting in 3 non-conservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

We have included 2 different sequences for the Ebola virus VP30 gene (SEQ ID NOS:4 and SEQ ID NO:7). Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS:20 and SEQ ID NO:23). As a result, the C-terminus of the VP30 protein differs significantly from that previously reported. In addition to these 2 changes, the VP30#2 gene in SEQ ID NO:23 contains a conservative transition from T to C at nt 9217. Because the primers originally used to clone the VP30 gene into the replicon were designed based on the GenBank sequence, the first clone that we constructed (SEQ ID NO:4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO:23) did not inhibit the ability of the protein to serve as a protective antigen in BALB/c mice. We are currently examining the ability of the new VEE replicon construct (SEQ ID NO:7), which we believe contains the authentic C-terminus of VP30 (VP30#2, SEQ ID NO:23), to protect mice against a lethal Ebola challenge.

The DNA sequence for Ebola virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO:21). The insertion of the T residue resulted in a change in the open reading frame of VP35 from that previously reported by Sanchez et al. (1993) following amino acid number 324. As a result, Ebola virus VP35 encodes for a protein of 340 amino acids, where amino acids 325 to 340 (SEQ ID NO:21) differ from and replace the C-terminal 27 amino acids of the previously published sequence.

Sequencing of VP30 and VP35 was also performed on RT/PCR products from RNA derived from cells that were infected with Ebola virus 1976, Ebola virus 1995 or the mouse-adapted Ebola virus. The changes noted above for the VRep constructs were also found in these Ebola viruses. Thus, we believe that these changes are real events and not artifacts of cloning.

The Ebola virus VP40 differed from the GenBank sequence by a transversion from a C to G at nt 4451 and a transition from a G to A at nt 5081. These sequence changes did not alter the protein sequence of VP40 (SEQ ID NO:22) from that of the published sequence.

To evaluate the protective efficacy of individual Ebola virus proteins and to determine whether the major histocompatibility (MHC) genes influence the immune response to Ebola virus antigens, two MHC-incompatible strains of mice were vaccinated with VRPs expressing an Ebola protein. As controls for these experiments, some mice were injected with VRPs expressing the nucleoprotein of Lassa virus or were injected with phosphate-buffered saline (PBS). Following Ebola virus challenge, the mice were monitored for morbidity and mortality, and the results are shown in Table 1.

The GP, NP, VP24, VP30, and VP40 proteins of Ebola virus generated either full or partial protection in BALB/c mice, and may therefore be beneficial components of a vaccine designed for human use. Vaccination with VRPs encoding the NP protein afforded the best protection. In this case, 100% of the mice were protected after three inoculations and 95% of the mice were protected after two inoculations. The VRP encoding VP24 also protected 90% to 95% of BALB/c mice against Ebola virus challenge. In separate experiments. (Table 2), two or three inoculations with VRPs encoding the VP24 protein protected BALB/c mice from a high dose ($1 \times 10^5$ plaque-forming units ($3 \times 10^6$ LD50)) of mouse-adapted Ebola virus.

Vaccination with VRPs encoding GP protected 52–70% of BALB/c mice. The lack of protection was not due to a failure to respond to the VRP encoding GP, as all mice had detectable Ebola virus-specific serum antibodies after vaccination.

Some protective efficacy was also observed in BALB/c mice vaccinated two or three times with VRPs expressing the VP30 protein (55% and 85%, respectively), or the VP40 protein (70% and 80%, respectively). The VP35 protein was not efficacious in the BALB/c mouse model, as only 20% and 26% of the mice were protected after either two or three doses, respectively.

Geometric mean titers of viremia were markedly reduced in BALB/c mice vaccinated with VRPs encoding Ebola virus proteins after challenge with Ebola virus, indicating an ability of the induced immune responses to reduce virus replication (Table 1A). In this study, immune responses to the GP protein were able to clear the virus to undetectable levels within 4 days after challenge in some mice.

When the same replicons were examined for their ability to protect C57BL/6 mice from a lethal challenge of Ebola virus, only the GP, NP, and VP35 proteins were efficacious (Table 1B). The best protection, 95% to 100%, was observed in C57BL/6 mice inoculated with VRPs encoding the GP protein. Vaccination with VRPs expressing NP protected 75% to 80% of the mice from lethal disease. In contrast to what was observed in the BALB/c mice, the VP35 protein was the only VP protein able to significantly protect the C57BL/6 mice. In this case, 3 inoculations with VRPs encoding VP35 protected 70% of the mice from Ebola virus challenge. The reason behind the differences in protection in the two mouse strains is not known but is believed to be due to the ability of the immunogens to sufficiently stimulate the cellular immune system. As with the BALB/c mice, the effects of the induced immune responses were also observed in reduced viremias and, occasionally, in a prolonged time to death of C57BL/6 mice.

VRPs expressing Ebola virus GP or NP were also evaluated for protective efficacy in a guinea pig model. Sera from vaccinated animals were assayed for antibodies to Ebola by western blotting, IFA, plaque-reduction neutralization, and ELISA. Vaccination with either VRP (GP or NP) induced high titers of antibodies to the Ebola proteins (Table 4) in both guinea pig strains. Neutralizing antibody responses were only detected in animals vaccinated with the VRP expressing GP (Table 4).

Vaccination of strain 2 inbred guinea pigs with the GP construct protected 3/5 animals against death from lethal Ebola challenge, and significantly prolonged the mean day of death in one of the two animals that died (Table 4). All of the strain 13 guinea pigs vaccinated with the GP construct, alone or in combination with NP, survived lethal Ebola challenge (Table 4). Vaccination with NP alone did not protect either guinea pig strain from challenge with the guinea pig-adapted Ebola virus.

To identify the immune mechanisms that mediate protection against Ebola virus and to determine whether antibodies are sufficient to protect against lethal disease, passive transfer studies were performed. One mL of immune sera, obtained from mice previously vaccinated with one of the Ebola virus VRPs, was passively administered to unvaccinated mice 24 hours before challenge with a lethal dose of mouse-adapted Ebola virus. Antibodies to GP, but not to NP or the VP proteins, protected mice from an Ebola virus challenge (Table 3). Antibodies to GP protected 75% of the BALB/c mice and 85% of the C57BL/6 mice from death. When the donor sera were examined for their ability to neutralize Ebola virus in a plaque-reduction neutralization assay, a 1:20 to 1:40 dilution of the GP-specific antisera reduced the number of viral plaque-forming units by at least 50% (data not shown). In contrast, antisera to the NP and VP proteins did not neutralize Ebola virus at a 1:20 or 1:40 dilution. These results are consistent with the finding that GP is the only viral protein found on the surface of Ebola virus, and is likely to induce virus-neutralizing antibodies.

Since the NP and VP proteins of Ebola virus are internal virion proteins to which antibodies are not sufficient for protection, it is likely that cytotoxic T lymphocytes (CTLs) are also important for protection against Ebola virus. Initial studies aimed at identifying cellular immune responses to individual Ebola virus proteins expressed from VRPs identified CTL responses to the VP24 and NP proteins (Table 5). One CTL epitope that we identified for the Ebola virus NP is recognized by C57BL/6 (H-$2^b$) mice, and has an amino acid sequence of, or contained within, the following 11 amino acids: VYQVNNLEEIC (SEQ ID NO:24). Vaccination with EboNPVRP and in vitro restimulation of spleen cells with this peptide consistently induces strong CTL responses in C57BL/6 (H-$2^b$) mice. In vivo vaccination to Ebola virus NP is required to detect the CTL activity, as evidenced by the failure of cells from C57BL/6 mice vaccinated with Lassa NP to develop lytic activity to peptide (SEQ ID NO:24) after in vitro restimulation with it. Specific lysis has been observed using very low effector:target ratios (<2:1). This CTL epitope is H-$2^b$ restricted in that it is not recognized by BALB/c (H-$2^d$) cells treated the same way (data not shown), and H-$2^b$ effector cells will not lyse MHC-mismatched target cells coated with this peptide.

A CTL epitope in the VP24 protein was also identified. It is recognized by BALB/c (H-$2^d$) mice, and has an amino acid sequence of, or contained within, the following 23 amino acids: LKFINKLDALLVVNYNGLLSSIF (SEQ ID NO:25). In the data shown in Table 5, high (>90%) specific lysis of P815 target cells coated with this peptide was observed. The background lysis of cells that were not peptide-coated was also high (>50%), which is probably due to the activity of natural killer cells. We are planning to repeat this experiment using the L5178Y target cells, which are not susceptible to natural killer cells.

Future studies will focus on determining the fine specificities of these CTL responses and the essential amino acids that constitute these CTL epitopes. Additional studies to identify other CTL epitopes on Ebola virus GP, NP, VP24, VP30, VP35, and VP40 will be performed. To evaluate the role of these CTLs in protection against Ebola virus, lymphocytes will be restimulated in vitro with peptides containing the CTL epitopes, and adoptively transferred into unvaccinated mice prior to Ebola virus challenge. In addition, future studies will examine the CTL responses to the other Ebola virus proteins to better define the roles of the cell mediated immune responses involved in protection against Ebola virus infection.

```
Sequence ID NO:1 (Ebola GP DNA sequence in replicon):

ATCGATAAGC TCGGAATTCG AGCTCGCCCG GGGATCCTCT AGAGTCGACA ACAACACAAT

GGGCGTTACA GGAATATTGC AGTTACCTCG TGATCGATTC AAGAGGACAT CATTCTTTCT

TTGGGTAATT ATCCTTTTCC AAAGAACATT TTCCATCCCA CTTGGAGTCA TCCACAATAG

CACATTACAG GTTAGTGATG TCGACAAACT AGTTTGTCGT GACAAACTGT CATCCACAAA

TCAATTGAGA TCAGTTGGAC TGAATCTCGA AGGGAATGGA GTGGCAACTG ACGTGCCATC

TGCAACTAAA AGATGGGGCT TCAGGTCCGG TGTCCCACCA AAGGTGGTCA ATTATGAAGC

TGGTGAATGG GCTGAAAACT GCTACAATCT TGAAATCAAA AAACCTGACG GGAGTGAGTG

TCTACCAGCA GCGCCAGACG GGATTCGGGG CTTCCCCCGG TGCCGGTATG TGCACAAAGT

ATCAGGAACG GGACCGTGTG CCGGAGACTT TGCCTTCCAT AAAGAGGGTG CTTTCTTCCT

GTATGATCGA CTTGCTTCCA CAGTTATCTA CCGAGGAACG ACTTTCGCTG AAGGTGTCGT

TGCATTTCTG ATACTGCCCC AAGCTAAGAA GGACTTCTTC AGCTCACACC CCTTGAGAGA

GCCGGTCAAT GCAACGGAGG ACCCGTCTAG TGGCTACTAT TCTACCACAA TTAGATATCA

GGCTACCGGT TTTGGAACCA ATGAGACAGA GTACTTGTTC GAGGTYGACA ATTTGACCTA
```

-continued

```
CGTCCAACTT GAATCAAGAT TCACACCACA GTTTCTGCTC CAGCTGAATG AGACAATATA
TACAAGTGGG AAAAGGAGCA ATACCACGGG AAAACTAATT TGGAAGGTCA ACCCCGAAAT
TGATACAACA ATCGGGGAGT GGGCCTTCTG GGAAACTAAA AAAAACCTCA CTAGAAAAAT
TCGCAGTGAA GAGTTGTCTT TCACAGTTGT ATCAAACGGA GCCAAAAACA TCAGTGGTCA
GAGTCCGGCG CGAACTTCTT CCGACCCAGG GACCAACACA ACAACTGAAG ACCACAAAAT
CATGGCTTCA GAAAATTCCT CTGCAATGGT TCAAGTGCAC AGTCAAGGAA GGGAAGCTGC
AGTGTCGCAT CTAACAACCC TTGCCACAAT CTCCACGAGT CCCCAATCCC TCACAACCAA
ACCAGGTCCG GACAACAGCA CCCATAATAC ACCCGTGTAT AAACTTGACA TCTCTGAGGC
AACTCAAGTT GAACAACATC ACCGCAGAAC AGACAACGAC AGCACAGCCT CCGACACTCC
CTCTGCCACG ACCGCAGCCG GACCCCCAAA AGCAGAGAAC ACCAACACGA GCAAGAGCAC
TGACTTCCTG GACCCCGCCA CCACAACAAG TCCCCAAAAC CACAGCGAGA CCGCTGGCAA
CAACAACACT CATCACCAAG ATACCGGAGA AGAGAGTGCC AGCAGCGGGA AGCTAGGCTT
AATTACCAAT ACTATTGCTG GAGTCGCAGG ACTGATCACA GGCGGGAGAA GAACTCGAAG
AGAAGCAATT GTCAATGCTC AACCCAAATG CAACCCTAAT TTACATTACT GGACTACTCA
GGATGAAGGT GCTGCAATCG GACTGGCCTG GATACCATAT TTCGGGCCAG CAGCCGAGGG
AATTTACATA GAGGGGCTAA TGCACAATCA AGATGGTTTA ATCTGTGGGT TGAGACAGCT
GGCCAACGAG ACGACTCAAG CTCTTCAACT GTTCCTGAGA GCCACAACTG AGCTACGCAC
CTTTTCAATC CTCAACCGTA AGGCAATTGA TTTCTTGCTG CAGCGATGGG GCGGCACATG
CCACATTCTG GGACCGGACT GCTGTATCGA ACCACATGAT TGGACCAAGA ACATAACAGA
CAAAATTGAT CAGATTATTC ATGATTTTGT TGATAAAACC CTTCCGGACC AGGGGGACAA
TGACAATTGG TGGACAGGAT GGAGACAATG GATACCGGCA GGTATTGGAG TTACAGGCGT
TGTAATTGCA GTTATCGCTT TATTCTGTAT ATGCAAATTT GTCTTTTAGT TTTTCTTCAG
ATTGCTTCAT GGAAAAGCTC AGCCTCAAAT CAATGAAACC AGGATTTAAT TATATGGATT
ACTTGAATCT AAGATTACTT GACAAATGAT AATATAATAC ACTGGAGCTT TAAACATAGC
CAATGTGATT CTAACTCCTT TAAACTCACA GTTAATCATA AACAAGGTTT GAGTCGACCT
GCAGCCAAGC TTATCGAT
```

Sequence ID NO:2 (Ebola NP DMA sequence in replicon):

```
ATCGATAAGC TTGGCTGCAG GTCGACTCTA GAGGATCCGA GTATGGATTC TCGTCCTCAG
AAAATCTGGA TGGCGCCGAG TCTCACTGAA TCTGACATGG ATTACCACAA GATCTTGACA
GCAGGTCTGT CCGTTCAACA GGGGATTGTT CGGCAAAGAQ TCATCCCAGT GTATCAAGTA
AACAATCTTG AAGAAATTTG CCAACTTATC ATACAGGCCT TGAAGCAGG TGTTGATTTT
CAAGAGAGTG CGGACAGTTT CCTTCTCATG CTTTGTCTTC ATCATGCGTA CCAGGGAGAT
TACAAACTTT TCTTGGAAAG TGGCGCAGTC AAGTATTTGG AAGGGCACGG GTTCCGTTTT
GAAGTCAAGA AGCGTGATGG AGTGAAGCGC CTTGAGGAAT TGCTGCCAGC AGTATCTAGT
GGAAAAAACA TTAAGAGAAC ACTTGCTGCC ATGCCGGAAG AGGAGACAAC TGAAGCTAAT
GCCGGTCAGT TTCTCTCCTT TGCAAGTCTA TTCCTTCCGA AATTGGTAGT AGGAGAAAAG
GCTTGCCTTG AGAAGGTTCA AAGGCAAATT CAAGTACATG CAGAGCAAGG ACTGATACAA
TATCCAACAG CTTGGCAATC AGTAGGACAC ATGATGGTGA TTTTCCGTTT GATGCGAACA
AATTTTCTGA TCAAATTTCT CCTAATACAC CAAGGGATGC ACATGGTTGC CGGGCATGAT
GCCAACGATG CTGTGATTTC AAATTCAGTG GCTCAAGCTC GTTTTTCAGG CTTATTGATT
```

```
GTCAAAACAG TACTTGATCA TATCCTACAA AAGACAGAAC GAGGAGTTCG TCTCCATCCT

CTTGCAAGGA CCGCCAAGGT AAAAAATGAG GTGAACTCCT TTAAGGCTGC ACTCAGCTCC

CTGGCCAAGC ATGGAGAGTA TGCTCCTTTC GCCCGACTTT TGAACCTTTC TGGAGTAAAT

AATCTTGAGC ATGGTCTTTT CCCTCAACTA TCGGCAATTG CACTCGGAGT CGCCACAGCA

CACGGGAGTA CCCTCGCAGG AGTAAATGTT GGAGAACAGT ATCAACAACT CAGAGAGGCT

GCCACTGAGG CTGAGAAGCA ACTCCAACAA TATGCAGAGT CTCGCGAACT TGACCATCTT

GGACTTGATG ATCAGGAAAA GAAAATTCTT ATGAACTTCC ATCAGAAAAA GAACGAAATC

AGCTTCCAGC AAACAAACGC TATGGTAACT CTAAGAAAAG AGCGCCTGGC CAAGCTGACA

GAAGCTATCA CTGCTGCGTC ACTGCCCAAA ACAAGTGGAC ATTACGATGA TGATGACGAC

ATTCCCTTTC CAGGACCCAT CAATGATGAC GACAATCCTG GCCATCAAGA TGATGATCCG

ACTGACTCAC AGGATACGAC CATTCCCGAT GTGGTGGTTG ATCCCGATGA TGGAAGCTAC

GGCGAATACC AGAGTTACTC GGAAAACGGC ATGAATGCAC CAGATGACTT GGTCCTATTC

GATCTAGACG AGGACGACGA GGACACTAAG CCAGTGCCTA ATAGATCGAC CAAGGGTGGA

CAACAGAAGA ACAGTCAAAA GGGCCAGCAT ATAGAGGGCA GACAGACACA ATCCAGGCCA

ATTCAAAATG TCCCAGGCCC TCACAGAACA ATCCACCACG CCAGTGCGCC ACTCACGGAC

AATGACAGAA GAAATGAACC CTCCGGCTCA ACCAGCCCTC GCATGCTGAC ACCAATTAAC

GAAGAGGCAG ACCCACTGGA CGATGCCGAC GACGAGACGT CTAGCCTTCC GCCCTTGGAG

TCAGATGATG AAGAGCAGGA CAGGGACGGA ACTTCCAACC GCACACCCAC TGTCGCCCCA

CCGGCTCCCG TATACAGAGA TCACTCTGAA AGAAAGAAC TCCCGCAAGA CGAGCAACAA

GATCAGGACC ACACTCAAGA GGCCAGGAAC CAGGACAGTG ACAACACCCA GTCAGAACAC

TCTTTTGAGG AGATGTATCG CCACATTCTA AGATCACAGG GGCCATTTGA TGCTGTTTTG

TATTATCATA TGATGAAGGA TGAGCCTGTA GTTTTCAGTA CCAGTGATGG CAAAGAGTAC

ACGTATCCAG ACTCCCTTGA AGAGGAATAT CCACCATGGC TCACTGAAAA AGAGGCTATG

AATGAAGAGA ATAGATTTGT TACATTGGAT GGTCAACAAT TTTATTGGCC GGTGATGAAT

CACAAGAATA AATTCATGGC AATCCTGCAA CATCATCAGT GAATGAGCAT GGAACAATGG

GATGATTCAA CCGACAAATA GCTAACATTA AGTAGTCCAG AACGAAAAC AGGAAGAATT

TTTGATGTCT AAGGTGTGAA TTATTATCAC AATAAAAGTG ATTCTTATTT TTGAATTTGG

GCGAGCTCGA ATTCCCGAGC TTATCGAT
```
Sequence ID NO:3 (Ebola VP24 DNA sequence in replicon):
```
ATCGATCTCC AGACACCAAG CAAGACCTGA GAAAAAACCA TGGCTAAAGC TACGGGACGA

TACAATCTAA TATCGCCCAA AAAGGACCTG GAGAAAGGGG TTGTCTTAAG CGACCTCTGT

AACTTCTTAG TTAGCCAAAC TATTCAGGGG TGGAAGGTTT ATTGGGCTGG TATTGAGTTT

GATGTGACTC ACAAAGGAAT GGCCCTATTG CATAGACTGA AAACTAATGA CTTTGCCCCT

GCATGGTCAA TGACAAGGAA TCTCTTTCCT CATTTATTTC AAAATCCGAA TTCCACAATT

GAATCACCGC TCTGGGCATT GAGAGTCATC CTTGCAGCAG GGATACAGGA CCAGCTGATT

GACCAGTCTT TGATTGAACC CTTAGCAGGA GCCCTTGGTC TGATCTCTGA TTGGCTGCTA

ACAACCAACA CTAACCATTT CAACATGCGA ACACAACGTG TCAAGGAACA ATTGAGGCTA

AAAATGCTGT CGTTGATTCG ATCCAATATT CTCAAGTTTA TTAACAAATT GGATGCTCTA

CATGTCGTGA ACTACAACGG ATTGTTGAGC AGTATTGAAA TTGGAACTCA AAATCATACA

ATCATCATAA CTCGAACTAA CATGGGTTTT CPGGTGGAGC TCCAAGAACC CGACAAATCG
```

-continued

GCAATGAACC GCATGAAGCC TGGGCCGGCG AAATTTTCCC TCCTTCATGA GTCCACACTG

AAAGCATTTA CACAAGGATC CTCGACACGA ATGCAAAGTT TCATTCTTGA ATTTAATAGC

TCTCTTGCTA TCTAACTAAG GTAGAATACT TCATATTGAG CTAACTCATA TATGCTGACT

CATCGAT

Sequence ID NO:4 Ebola VP30 DNA sequence in replicon):

ATCGATCAGA TCTGCGAACC GGTAGAGTTT AGTTGCAACC TAACACACAT AAAGCATTGG

TCAAAAAGTC AATAGAAATT TAAACAGTGA GTGGAGACAA CTTTTAAATG GAAGCTTCAT

ATGAGAGAGG ACGCCCACGA GCTGCCAGAC AGCATTCAAG GGATGGACAC GACCACCATG

TTCGAGCACG ATCATCATCC AGAGAGAATT ATCGAGGTGA GTACCGTCAA TCAAGGAGCG

CCTCACAAGT GCGCGTTCCT ACTGTATTTC ATAAGAAGAG AGTTGAACCA TTAACAGTTC

CTCCAGCACC TAAAGACATA TGTCCGACCT TGAAAAAAGG ATTTTTGTGT GACAGTAGTT

TTTGCAAAAA AGATCACCAG TTGGAGAGTT TAACTGATAG GGAATTACTC CTACTAATCG

CCCGTAAGAC TTGTGGATCA GTAGAACAAC AATTAAATAT AACTGCACCC AAGGACTCGC

GCTTAGCAAA TCCAACGGCT GATGATTTCC AGCAAGAGGA AGGTCCAAAA ATTACCTTGT

TGACACTGAT CAAGACGGCA GAACACTGGG CGAGACAAGA CATCAGAACC ATAGAGGATT

CAAAATTAAG AGCATTGTTG ACTCTATGTG CTGTGATGAC GAGGAAATTC TCAAAATCCC

AGCTGAGTCT TTTATGTGAG ACACACCTAA GGCGCGAGGG GCTTGGGCAA GATCAGGCAG

AACCCGTTCT CGAAGTATAT CAACGATTAC ACAGTGATAA AGGAGGCAGT TTTGAAGCTG

CACTATGGCA ACAATGGGAC CTACAATCCC TAATTATGTT TATCACTGCA TTCTTGAATA

TTGCTCTCCA GTTACCGTGT GAAAGTTCTG CTGTCGTTGT TTCAGGGTTA AGAACATTGG

TTCCTCAATC AGATAATGAG GAAGCTTCAA CCAACCCGGG GACATGCTCA TGGTCTGATG

AGGGTACATC GAT

Sequence ID NO:5 (Ebola VP35 DNA sequence in replicon):

ATCGATAGAA AAGCTGGTCT AACAAGATGA CAACTAGAAC AAAGGGCAGG GGCCATACTG

CGGCCACGAC TCAAAACGAC AGAATGCCAG GCCCTGAGCT TTCGGGCTGG ATCTCTGAGC

AGCTAATGAC CGGAAGAATT CCTGTAAGCG ACATCTTCTG TGATATTGAG AACAATCCAG

GATTATGCTA CGCATCCCAA ATGCAACAAA CGAAGCCAAA CCCGAAGACG CGCAACAGTC

AAACCCAAAC GGACCCAATT TGCAATCATA GTTTTGAGGA GGTAGTACAA ACATTGGCTT

CATTGGCTAC TGTTGTGCAA CAACAAACCA TCGCATCAGA ATCATTAGAA CAACGCATTA

CGAGTCTTGA GAATGGTCTA AAGCCAGTTT ATGATATGGC AAAAACAATC TCCTCATTGA

ACAGGGTTTG TGCTGAGATG GTTGCAAAAT ATGATCTTCT GGTGATGACA ACCGGTCGGG

CAACAGCAAC CGCTGCGGCA ACTGAGGCTT ATTGGGCCGA ACATGCTCAA CCACCACCTG

GACCATCACT TTATGAAGAA AGTGCGATTC GGGGTAAGAT TGAATCTAGA GATGAGACCG

TCCCTCAAAG TGTTAGGGAG GCATTCAACA ATCTAAACAG TACCACTTCA CTAACTGAGG

AAAATTTTGG GAAACCTGAC ATTTCGGCAA AGGATTTGAG AAACATTATG TATGATCACT

TGCCTGGTTT TGGAACTGCT TTCCACCAAT TAGTACAAGT GATTTGTAAA TTGGGAAAAG

ATAGCAACTC ATTGGACATC ATTCATGCTG AGTTCCAGGC CAGCCTGGCT GAAGGAGACT

CTCCTCAATG TGCCCTAATT CAAATTACAA AAAGAGTTCC AATCTTCCAA GATGCTGCTC

CACCTGTCAT CCACATCCGC TCTCGAGGTG ACATTCCCCG AGCTTGCCAG AAAAGCTTGC

GTCCAGTCCC ACCATCGCCC AAGATTGATC GAGGTTGGGT ATGTGTTTTT CAGCTTCAAG

```
ATGGTAAAAC ACTTGGACTC AAAATTTGAG CCAATCTCCC TTCCCTCCGA AAGAGGCGAA

TAATAGCAGA GGCTTCAACT GCTGAACTAT AGGGTACGTT ACATTAATGA TACACTTGTG

AGATCGAT
```

Sequence ID NO:6 (Ebola VP40 DNA sequence in replicon):

```
ATCGATCCTA CCTCGGCTGA GAGAGTGTTT TTTCATTAAC CTTCATCTTG TAAACGTTGA

GCAAAATTGT TAAAAATATG AGGCGGGTTA TATTGCCTAC TGCTCCTCCT GAATATATGG

AGGCCATATA CCCTGTCAGG TCAAATTCAA CAATTGCTAG AGGTGGCAAC AGCAATACAG

GCTTCCTGAC ACCGGAGTCA GTCAATGGGG ACACTCCATC GAATCCACTC AGGCCAATTG

CCGATGACAC CATCGACCAT GCCAGCCACA CACCAGGCAG TGTGTCATCA GCATTCATCC

TTGAAGCTAT GGTGAATGTC ATATCGGGCC CCAAAGTGCT AATGAAGCAA ATTCAATTT

GGCTTCCTCT AGGTGTCGCT GATCAAAAGA CCTACAGCTT TGACTCAACT ACGGCCGCCA

TCATGCTTGC TTCATACACT ATCACCCATT TCGGCAAGGC AACCAATCCA CTTGTCAGAG

TCAATCGGCT GGGTCCTGGA ATCCCGGATC ATCCCCTCAG GCTCCTGCGA ATTGGAAACC

AGGCTTTCCT CCAGGAGTTC GTTCTTCCGC CAGTCCAACT ACCCCAGTAT TTCACCTTTG

ATTTGACAGC ACTCAAACTG ATCACCCAAC CACTGCCTGC TGCAACATGG ACCGATGACA

CTCCAACAGG ATCAAATGGA GCGTTGCGTC CAGGAATTTC ATTTCATCCA AAACTTCGCC

CCATTCTTTT ACCCAACAAA AGTGGGAAGA AGGGGAACAG TGCCGATCTA ACATCTCCGG

AGAAAATCCA AGCAATAATG ACTTCACTCC AGGACTTTAA GATCGTTCCA ATTGATCCAA

CCAAAAATAT CATGGGAATC GAAGTGCCAG AAACTCTGGT CCACAAGCTG ACCGGTAAGA

AGGTGACTTC TAAAAATGGA CAACCAATCA TCCCTGTTCT TTTGCCAAAG TACATTGGGT

TGGACCCGGT GGCTCCAGGA GACCTCACCA TGGTAATCAC ACAGGATTGT GACACGTGTC

ATTCTCCTGC AAGTCTTCCA GCTGTGATTG AGAAGTAATT GCAATAATTG ACTCAGATCC

AGTTTTATAG AATCTTCTCA GGGATAGTGC ATAACATATC GAT
```

Sequence ID NO:7 (Ebola VP30(#2) DNA sequence in replicon):

```
ATCGATCAGA TCTGCGAACC GGTAGAGTTT AGTTGCAACC TAACACACAT AAAGCATTGG

TCAAAAAGTC AATAGAAATT TAAACAGTGA GTGGAGACAA CTTTTAAATG GAAGCTTCAT

ATGAGAGAGG ACGCCCACGA GCTGCCAGAC AGCATTCAAG GGATGGACAC GACCACCATG

TTCGAGCACG ATCATCATCC AGAGAGAATT ATCGAGGTGA GTACCGTCAA TCAAGGAGCG

CCTCACAAGT GCGCGTTCCT ACTGTATTTC ATAAGAAGAG AGTTGAACCA TTAACAGTTC

CTCCAGCACC TAAAGACATA TGTCCGACCT TGAAAAAAGG ATTTTTGTGT GACAGTAGTT

TTTGCAAAAA AGATCACCAG TTGGAGAGTT TAACTGATAG GGAATTACTC CTACTAATCG

CCCGTAAGAC TTGTGGATCA GTAGAACAAC AATTAAATAT AACTGCACCC AAGGACTCGC

GCTTAGCAAA TCCAACGGCT GATGATTTCC AGCAAGAGGA AGGTCCAAAA ATTACCTTGT

TGACACTGAT CAAGACGGCA GAACACTGGG CGAGACAAGA CATCAGAACC ATAGAGGATT

CAAAATTAAG AGCATTGTTG ACTCTATGTG CTGTGATGAC GAGGAAATTC TCAAAATCCC

AGCTGAGTCT TTTATGTGAG ACACACCTAA GGCGCGAGGG GCTTGGGCAA GATCAGGCAG

AACCCGTTCT CGAAGTATAT CAACGATTAC ACAGTGATAA GGAGGCAGT TTGAAGCTG

CACTATGGCA ACAATGGGAC CGACAATCCC TAATCATGTT TATCACTGCA TTCTTGAATA

TTGCTCTCCA GTTACCGTGT GAAAGTTCTG CTGTCGTTGT TCAGGGTTA AGAACATTGG

TTCCTCAATC AGATAATGAG GAAGCTTCAA CCAACCCGGG GACATGCTCA TGGTCTGATG
```

-continued

```
AGGGTACCCC TTAATAAGGC TGACTAAAAC ACTATATAAC CTTCTACTTG ATCACAATAC

TCCGTATACC TATCATCATA TATTTAATCA AGACGATATC CTTTAAAACT TATTCAGTAC

TATAATCACT CTCGTTTCAA ATTAATAAGA TGTGCATGAT TGCCCTAATA TATGAAGAGG

TATGATACAA CCCTAACAGA TCGAT
```

Sequence ID NO:8 (Ebola VP24 forward primer):

5'-GGGATCGATCTCCAGACACCAAGCAAGACC-3'

Sequence ID NO:9 (Ebola VP24 reverse primer):

5'-GGGATCGATGAGTCAGCATATATGAGTTAGCTC-3'

Sequence ID NO:10 (Ebola VP30 forward primer):

5'-CCCATCGATCAGATCTGCGAACCGGTAGAG-3'

Sequence ID NO:11 (Ebola VP30 reverse primer):

5'-CCCATCGATGTACCCTCATCAGACCATGAGC-3'

Sequence ID NO:12 (Ebola VP35 forward primer):

5'-GGGATCGATAGAAAAGCTGGTCTAACAAGATGA-3'

Sequence ID NO:13 (Ebola VP35 reverse primer):

5'-CCCATCGATCTCACAAGTGTATCATTAATGTAACGT-3'

Sequence ID NO:14 (Ebola VP40 forward primer):

5'-CCCATCGATCCTACCTCGGCTGAGAGAGTG-3'

Sequence ID NO:15 (Ebola VP40 reverse primer):

5'-CCCATCGATATGTTATGCACTATCCCTGAGAAG-3'

Sequence ID NO:16 (Ebola VP30#2 reverse primer):

5'-CCC ATC GAT CTG TTA GGG TTG TAT CATACC-3'

Sequence ID NO:17 (Ebola GP amino acid sequence from replicon):

Met Gly Val Thr Gly Ile Leu Gln Leu Pro Arg Asp Arg Phe Lys Arg Thr Ser
Phe Phe Leu Trp Val Ile Ile Leu Phe Gln Arg Thr Phe Ser Ile Pro Leu Gly
Val Ile His Asn Ser Thr Leu Gln Val Ser Asp Val Asp Lys Leu Val Cys Arg
Asp Lys Leu Ser Ser Thr Asn Gln Leu Arg Ser Val Gly Leu Asn Leu Glu Gly
Asn Gly Val Ala Thr Asp Val Pro Ser Ala Thr Lys Arg Trp Gly Phe Arg Ser
Gly Val Pro Pro Eqs Val Val Asn Tyr Glu Ala Gly Glu Trp Ala Glu Asn Cys
Tyr Asn Leu Glu Ile Lys Lys Pro Asp Gly Ser Glu Cys Leu Pro Ala Ala Pro
Asp Gly Ile Arg Gly Phe Pro Arg Cys Arg Tyr Val His Lys Val Ser Gly Thr
Gly Pro Cys Ala Gly Asp Phe Ala Phe His Lys Glu Gly Ala Phe Phe Leu Tyr
Asp Arg Leu Ala Ser Thr Val Ile Tyr Arg Gly Thr Thr Phe Ala Glu Gly Val
Val Ala Phe Leu Ile Leu Pro Gln Ala Lys Lys Asp Phe Phe Ser Ser His Pro
Leu Arg Glu Pro Val Asn Ala Thr Glu Asp Pro Ser Ser Gly Tyr Tyr Ser Thr
Thr Ile Arg Tyr Gln Ala Thr Gly Phe Gly Thr Asn Glu Thr Glu Tyr Leu Phe
Glu Val Asp Asn Leu Thr Tyr Val Gln Leu Glu Ser Arg Phe Thr Pro Gln Phe
Leu Leu Gln Leu Asn Glu Thr Ile Tyr Thr Ser Gly Lys Arg Ser Asn Thr Thr
Gly Lys Leu Ile Trp Lys Val Asn Pro Glu Ile Asp Thr Thr Ile Gly Glu Trp
Ala Phe Trp Glu Thr Lys Lys Asn Leu Thr Arg Lys Ile Arg Ser Glu Glu Leu

-continued

Ser Phe Thr Val Val Ser Asn Gly Ala Lys Asn Ile Ser Gly Gln Ser Pro Ala
Arg Thr Ser Ser Asp Pro Gly Thr Asn Thr Thr Thr Glu Asp His Lys Ile Met
Ala Ser Glu Asn Ser Ser Ala Met Val Gln Val His Ser Gln Gly Arg Glu Ala
Ala Val Ser His Leu Thr Thr Leu Ala Thr Ile Ser Thr Ser Pro Gln Ser Leu
Thr Thr Lys Pro Gly Pro Asp Asn Ser Thr His Asn Thr Pro Val Tyr Lys Leu
Asp Ile Ser Glu Ala Thr Gln Val Glu Gln His His Arg Arg Thr Asp Asn Asp
Ser Thr Ala Ser Asp Thr Pro Ser Ala Thr Thr Ala Ala Gly Pro Pro Lys Ala
Glu Asn Thr Asn Thr Ser Lys Ser Thr Asp Phe Leu Asp Pro Ala Thr Thr Thr
Ser Pro Gln Asn His Ser Glu Thr Val Gly Asn Asn Thr His His Gln Asp
Thr Gly Glu Glu Ser Ala Ser Ser Gly Lys Leu Gly Leu Ile Thr Asn Thr Ile
Ala Gly Val Ala Gly Leu Ile Thr Gly Gly Arg Arg Thr Arg Arg Glu Ala Ile
Val Asn Ala Gln Pro Lys Cys Asn Pro Asn Leu His Tyr Trp Thr Thr Gln Asp
Glu Gly Ala Ala Ile Gly Leu Ala Trp Ile Pro Tyr Phe Gly Pro Ala Ala Glu
Gly Ile Tyr Ile Glu Gly Leu Met His Asn Gln Asp Gly Leu Ile Cys Gly Leu
Arg Gln Leu Ala Asn Glu Thr Thr Gln Ala Leu Gln Leu Phe Leu Arg Ala Thr
Thr Glu Leu Arg Thr Phe Ser Ile Leu Asn Arg Lys Ala Ile Asp Phe Leu Leu
Gln Arg Trp Gly Gly Thr Cys His Ile Leu Gly Pro Asp Cys Cys Ile Glu Pro
His Asp Trp Thr Lys Asn Ile Thr Asp Lys Ile Asp Gln Ile Ile His Asp Phe
Val Asp Lys Thr Leu Pro Asp Gln Gly Asp Asn Asp Asn Trp Trp Thr Gly Trp
Arg Gln Trp Ile Pro Ala Gly Ile Gly Val Thr Gly Val Val Ile Ala Val Ile
Ala Leu Phe Cys Ile Cys Lys Phe Val Phe *

Sequence ID NO:18 (Ebola NP amino acid sequence from replicon):
Met Asp Ser Arg Pro Gln Lys Ile Trp Met Ala Pro Ser Leu Thr Glu Ser Asp
Met Asp Tyr His Lys Ile Leu Thr Ala Gly Leu Ser Val Gln Gln Gly Ile Val
Arg Gln Arg Val Ile Pro Val Tyr Gln Val Asn Asn Leu Glu Glu Ile Cys Gln
Leu Ile Ile Gln Ala Phe Glu Ala Gly Val Asp Phe Gln Glu Ser Ala Asp Ser
Phe Leu Leu Met Leu Cys Leu His His Ala Tyr Gln Gly Asp Tyr Lys Leu Phe
Leu Glu Ser Gly Ala Val Lys Tyr Leu Glu Gly His Gly Phe Arg Phe Glu Val
Lys Lys Arg Asp Gly Val Lys Arg Leu Glu Glu Leu Leu Pro Ala Val Ser Ser
Gly Lys Asn Ile Lys Arg Thr Leu Ala Ala Met Pro Glu Glu Glu Thr Thr Glu
Ala Asn Ala Gly Gln Phe Leu Ser Phe Ala Ser Leu Phe Leu Pro Lys Leu Val
Val Gly Glu Lys Ala Cys Leu Glu Lys Val Gln Arg Gln Ile Gln Val His Ala
Glu Gln Gly Leu Ile Gln Tyr Pro Thr Ala Trp Gln Ser Val Gly His Met Met
Val Ile Phe Arg Leu Met Arg Thr Asn Phe Leu Ile Lys Phe Leu Leu Ile His
Gln Gly Met His Met Val Ala Gly His Asp Ala Asn Asp Ala Val Ile Ser Asn
Ser Val Ala Gln Ala Arg Phe Ser Gly Leu Leu Ile Val Lys Thr Val Leu Asp
His Ile Leu Gln Lys Thr Glu Arg Gly Val Arg Leu His Pro Leu Ala Arg Thr
Ala Lys Val Lys Asn Glu Val Asn Ser Phe Lys Ala Ala Leu Ser Ser Leu Ala
Lys His Gly Glu Tyr Ala Pro Phe Ala Arg Leu Leu Asn Leu Ser Gly Val Asn
Asn Leu Glu His Gly Leu Phe Pro Gln Leu Ser Ala Ile Ala Leu Gly Val Ala -continued

```
Thr Ala His Gly Ser Thr Leu Ala Gly Val Asn Val Gly Glu Gln Tyr Gln Gln
Leu Arg Glu Ala Ala Thr Glu Ala Glu Lys Gln Leu Gln Gln Tyr Ala Glu Ser
Arg Glu Leu Asp His Leu Gly Leu Asp Asp Gln Glu Lys Lys Ile Leu Met Asn
Phe His Gln Lys Lys Asn Glu Ile Ser Phe Gln Gln Thr Asn Ala Met Val Thr
Leu Arg Lys Glu Arg Leu Ala Lys Leu Thr Glu Ala Ile Thr Ala Ala Ser Leu
Pro Lys Thr Ser Gly His Tyr Asp Asp Asp Asp Ile Pro Phe Pro Gly Pro
Ile Asn Asp Asp Asp Asn Pro Gly His Gln Asp Asp Asp Pro Thr Asp Ser Gln
Asp Thr Thr Ile Pro Asp Val Val Val Asp Pro Asp Asp Gly Ser Tyr Gly Glu
Tyr Gln Ser Tyr Ser Glu Asn Gly Met Asn Ala Pro Asp Asp Leu Val Leu Phe
Asp Leu Asp Glu Asp Asp Glu Asp Thr Lys Pro Val Pro Asn Arg Ser Thr Lys
Gly Gly Gln Gln Lys Asn Ser Gln Lys Gly Gln His Ile Glu Gly Arg Gln Thr
Gln Ser Arg Pro Ile Gln Asn Val Pro Gly Pro His Arg Thr Ile His His Ala
Ser Ala Pro Leu Thr Asp Asn Asp Arg Arg Asn Glu Pro Ser Gly Ser Thr Ser
Pro Arg Met Leu Thr Pro Ile Asn Glu Glu Ala Asp Pro Leu Asp Asp Ala Asp
Asp Glu Thr Ser Ser Leu Pro Pro Leu Glu Ser Asp Asp Glu Glu Gln Asp Arg
Asp Gly Thr Ser Asn Arg Thr Pro Thr Val Ala Pro Pro Ala Pro Val Tyr Arg
Asp His Ser Glu Lys Lys Glu Leu Pro Gln Asp Glu Gln Gln Asp Gln Asp His
Thr Gln Glu Ala Arg Asn Gln Asp Ser Asp Asn Thr Gln Ser Glu His Ser Phe
Glu Glu Met Tyr Arg His Ile Leu Arg Ser Gln Gly Pro Phe Asp Ala Val Leu
Tyr Tyr His Met Met Lys Asp Glu Pro Val Val Phe Ser Thr Ser Asp Gly Lys
Glu Tyr Thr Tyr Pro Asp Ser Leu Glu Glu Glu Tyr Pro Pro Trp Leu Thr Glu
Lys Glu Ala Met Asn Glu Glu Asn Arg Phe Val Thr Leu Asp Gly Gln Gln Phe
Tyr Trp Pro Val Met Asn His Lys Asn Lys Phe Met Ala Ile Leu Gln His His
Gln *
```

Sequence ID NO:19 (Ebola VP24 amino acid sequence from replicon):

```
Met Ala Lys Ala Thr Gly Arg Tyr Asn Leu Ile Ser Pro Lys Lys Asp Leu Glu
Lys Gly Val Val Leu Ser Asp Leu Cys Asn Phe Leu Val Ser Gln Thr Ile Gln
Gly Trp Lys Val Tyr Trp Ala Gly Ile Glu Phe Asp Val Thr His Lys Gly Met
Ala Leu Leu His Arg Leu Lys Thr Asn Asp Phe Ala Pro Ala Trp Ser Met Thr
Arg Asn Leu Phe Pro His Leu Phe Gln Asn Pro Asn Ser Thr Ile Glu Ser Pro
Leu Trp Ala Leu Arg Val Ile Leu Ala Ala Gly Ile Gln Asp Gln Leu Ile Asp
Gln Ser Leu Ile Glu Pro Leu Ala Gly Ala Leu Gly Leu Ile Ser Asp Trp Leu
Leu Thr Thr Asn Thr Asn His Phe Asn Met Arg Thr Gln Arg Val Lys Glu Gln
Leu Ser Leu Lys Met Leu Ser Leu Ile Arg Ser Asn Ile Leu Lys Phe Ile Asn
Lys Leu Asp Ala Leu His Val Val Asn Tyr Asn Gly Leu Leu Ser Ser Ile Glu
Ile Gly Thr Gln Asn His Thr Ile Ile Thr Arg Thr Asn Met Gly Phe Leu
Val Glu Leu Gln Glu Pro Asp Lys Ser Ala Met Asn Arg Met Lys Pro Gly Pro
Ala Lys Phe Ser Leu Leu His Glu Ser Thr Leu Lys Ala Phe Thr Gln Gly Ser
Ser Thr Arg Met Gln Ser Leu Ile Leu Glu Phe Asn Ser Ser Leu Ala Ile *
```

Sequence ID NO:20 (Ebola VP30 amino acid sequence from replicon):

-continued

Met Glu Ala Ser Tyr Glu Arg Gly Arg Pro Arg Ala Arg Gln His Ser Arg
Asp Gly His Asp His His Val Arg Ala Arg Ser Ser Arg Glu Asn Tyr Arg
Gly Glu Tyr Arg Gln Ser Arg Ser Ala Ser Gln Val Arg Val Pro Thr Val Phe
His Lys Lys Arg Val Glu Pro Leu Thr Val Pro Pro Ala Pro Lys Asp Ile Cys
Pro Thr Leu Lys Lys Gly Phe Leu Cys Asp Ser Ser Phe Cys Lys Lys Asp His
Gln Leu Glu Ser Leu Thr Asp Arg Glu Leu Leu Leu Leu Ile Ala Arg Lys Thr
Cys Gly Ser Val Glu Gln Gln Leu Asn Ile Thr Ala Pro Lys Asp Ser Arg Leu
Ala Asn Pro Thr Ala Asp Asp Phe Gln Gln Glu Glu Gly Pro Lys Ile Thr Leu
Leu Thr Leu Ile Lys Thr Ala Glu His Trp Ala Arg Gln Asp Ile Arg Thr Ile
Glu Asp Ser Lys Leu Arg Ala Leu Leu Thr Leu Cys Ala Val Met Thr Arg Lys
Phe Ser Lys Ser Gln Leu Ser Leu Leu Cys Glu Thr His Leu Arg Arg Glu Gly
Leu Gly Gln Asp Gln Ala Glu Pro Val Leu Glu Val Tyr Gln Arg Leu His Ser
Asp Lys Gly Gly Ser Phe Glu Ala Ala Leu Trp Gln Gln Trp Asp Leu Gln Ser
Leu Ile Met Phe Ile Thr Ala Phe Leu Asn Ile Ala Leu Gln Leu Pro Cys Glu
Ser Ser Ala Val Val Val Ser Gly Leu Arg Thr Leu Val Pro Gln Ser Asp Asn
Glu Glu Ala Ser Thr Asn Pro Gly Thr Cys Ser Trp Ser Asp Glu Gly Thr Ser
Ile Gln Gln Gln Leu Ala Ser Cys Leu His Arg Thr Arg Gly Asp Trp His Ala
Ala Leu Lys Phe Leu Phe Tyr Phe Ser Phe Leu Phe Arg Ile Gly Phe Cys Phe
*

Sequence ID NO:21 (Ebola VP35 amino acid sequence from replicon):
Met Thr Thr Arg Thr Lys Gly Arg Gly His Thr Ala Ala Thr Thr Gln Asn Asp
Arg Met Pro Gly Pro Glu Leu Ser Gly Trp Ile Ser Glu Gln Leu Met Thr Gly
Arg Ile Pro Val Ser Asp Ile Phe Cys Asp Ile Glu Asn Asn Pro Gly Leu Cys
Tyr Ala Ser Gln Met Gln Gln Thr Lys Pro Asn Pro Lys Thr Arg Asn Ser Gln
Thr Gln Thr Asp Pro Ile Cys Asn His Ser Phe Glu Glu Val Val Gln Thr Leu
Ala Ser Leu Ala Thr Val Val Gln Gln Gln Thr Ile Ala Ser Glu Ser Leu Glu
Gln Arg Ile Thr Ser Leu Glu Asn Gly Leu Lys Pro Val Tyr Asp Met Ala Lys
Thr Ile Ser Ser Leu Asn Arg Val Cys Ala Glu Met Val Ala Lys Tyr Asp Leu
Leu Val Met Thr Thr Gly Arg Ala Thr Ala Thr Ala Ala Ala Thr Glu Ala Tyr
Trp Ala Glu His Gly Gln Pro Pro Pro Gly Pro Ser Leu Tyr Glu Glu Ser Ala
Ile Arg Gly Lys Ile Glu Ser Arg Asp Glu Thr Val Pro Gln Ser Val Arg Glu
Ala Phe Asn Asn Leu Asn Ser Thr Thr Ser Leu Thr Glu Glu Asn Phe Gly Lys
Pro Asp Ile Ser Ala Lys Asp Leu Arg Asn Ile Met Tyr Asp His Leu Pro Gly
Phe Gly Thr Ala Phe His Gln Leu Val Gln Val Ile Cys Lys Leu Gly Lys Asp
Ser Asn Ser Leu Asp Ile Ile His Ala Glu Phe Gln Ala Ser Leu Ala Glu Gly
Asp Ser Pro Gln Cys Ala Leu Ile Gln Ile Thr Lys Arg Val Pro Ile Phe Gln
Asp Ala Ala Pro Pro Val Ile His Ile Arg Ser Arg Gly Asp Ile Pro Arg Ala
Cys Gln Lys Ser Leu Arg Pro Val Pro Pro Ser Pro Lys Ile Asp Arg Gly Trp
Val Cys Val Phe Gln Leu Gln Asp Gly Lys Thr Leu Gly Leu Lys Ile *

Sequence ID NO:22 (Ebola VP40 amino acid sequence from replicon):

-continued

Met Arg Arg Val Ile Leu Pro Thr Ala Pro Pro Glu Tyr Met Glu Ala Ile Tyr
Pro Val Arg Ser Asn Ser Thr Ile Ala Arg Gly Gly Asn Ser Asn Thr Gly Phe
Leu Thr Pro Glu Ser Val Asn Gly Asp Thr Pro Ser Asn Pro Leu Arg Pro Ile
Ala Asp Asp Thr Ile Asp His Ala Ser His Thr Pro Gly Ser Val Ser Ser Ala
Phe Ile Leu Glu Ala Met Val Asn Val Ile Ser Gly Pro Lys Val Leu Met Lys
Gln Ile Pro Ile Trp Leu Pro Leu Gly Val Ala Asp Gln Lys Thr Tyr Ser Phe
Asp Ser Thr Thr Ala Ala Ile Met Leu Ala Ser Tyr Thr Ile Thr His Phe Gly
Lys Ala Thr Asn Pro Leu Val Arg Val Asn Arg Leu Gly Pro Gly Ile Pro Asp
His Pro Leu Arg Leu Leu Arg Ile Gly Asn Gln Ala Phe Leu Gln Glu Phe Val
Leu Pro Pro Val Gln Leu Pro Gln Tyr Phe Thr Phe Asp Leu Thr Ala Leu Lys
Leu Ile Thr Gln Pro Leu Pro Ala Ala Thr Trp Thr Asp Asp Thr Pro Thr Gly
Ser Asn Gly Ala Leu Arg Pro Gly Ile Ser Phe His Pro Lys Leu Arg Pro Ile
Leu Leu Pro Asn Lys Ser Gly Lys Lys Gly Asn Ser Ala Asp Leu Thr Ser Pro
Glu Lys Ile Gln Ala Ile Met Thr Ser Leu Gln Asp Phe Lys Ile Val Pro Ile
Asp Pro Thr Lys Asn Ile Met Gly Ile Glu Val Pro Glu Thr Leu Val His Lys
Leu Thr Gly Lys Lys Val Thr Ser Lys Asn Gly Gln Pro Ile Ile Pro Val Leu
Leu Pro Lys Tyr Ile Gly Leu Asp Pro Val Ala Pro Gly Asp Leu Thr Met Val
Ile Thr Gln Asp Cys Asp Thr Cys His Ser Pro Ala Ser Leu Pro Ala Val Ile
Glu Lys *

Sequence ID NO:23 (new Ebola VP30 F2 amino acid sequence from replicon):

Met Glu Ala Ser Tyr Glu Arg Gly Arg Pro Arg Ala Ala Arg Gln His Ser Arg
Asp Gly His Asp His His Val Arg Ala Arg Ser Ser Ser Arg Glu Asn Tyr Arg
Gly Glu Tyr Arg Gln Ser Arg Ser Ala Ser Gln Val Arg Val Pro Thr Val Phe
His Lys Lys Arg Val Glu Pro Leu Thr Val Pro Pro Ala Pro Lys Asp Ile Cys
Pro Thr Leu Lys Lys Gly Phe Lou Cys Asp Ser Ser Phe Cys Lys Lys Asp His
Gln Leu Glu Ser Leu Thr Asp Arg Glu Leu Leu Leu Leu Ile Ala Arg Lys Thr
Cys Gly Ser Val Glu Gln Gln Leu Asn Ile Thr Ala Pro Lys Asp Ser Arg Leu
Ala Asn Pro Thr Ala Asp Asp Phe Gln Gln Glu Glu Gly Pro Lys Ile Thr Leu
Leu Thr Leu Ile Lys Thr Ala Glu His Trp Ala Arg Gln Asp Ile Arg Thr Ile
Glu Asp Ser Lys Leu Arg Ala Leu Leu Thr Leu Cys Ala Val Met Thr Arg Lys
Phe Ser Lys Ser Gln Leu Ser Leu Leu Cys Glu Thr His Leu Arg Arg Glu Gly
Leu Gly Gln Asp Gln Ala Glu Pro Val Leu Glu Val Tyr Gln Arg Leu His Ser
Asp Lys Gly Gly Ser Phe Glu Ala Ala Leu Trp Gln Gln Trp Asp Arg Gln Ser
Leu Ile Met Phe Ile Thr Ala Phe Leu Asn Ile Ala Leu Gln Leu Pro Cys Glu
Ser Ser Ala Val Val Val Ser Gly Leu Arg Thr Leu Val Pro Gln Ser Asp Asn
Glu Glu Ala Ser Thr Asn Pro Gly Thr Cys Ser Trp Ser Asp Glu Gly Thr Pro
*

```
Sequence ID NO:24 (Ebola NP CTL epitope):

VYQVNNLEEIC

Sequence ID NO:25 (Ebola VP24 CTL epitope):

LKFINKLDALLVVNYNGLLSSIF
```

What is claimed is:

1. The recombinant DNA construct designated VRepEboVP35, having ATCC® accession number PTA-5649.

2. The self replicating RNA produced from the construct of claim 1.

3. Infectious alphavirus particles comprising the self replicating RNA of claim 2.

4. A method for producing Ebola virus proteins comprising culturing cells transformed with the DNA construct of claim 1, under conditions such that at least one DNA fragment encoding Ebola proteins is expressed and Ebola proteins are produced.

* * * * *